United States Patent
Sawhney et al.

(10) Patent No.: US 8,852,230 B2
(45) Date of Patent: Oct. 7, 2014

(54) APPARATUS AND METHODS FOR SEALING A VASCULAR PUNCTURE

(75) Inventors: Amarpreet S. Sawhney, Lexington, MA (US); Farhad Khosravi, Los Altos Hills, CA (US); Suresh S. Pai, Mountain View, CA (US); Scott R. Sershen, Redwood City, CA (US)

(73) Assignee: Incept LLC, Lexington, MA (US)

( * ) Notice: Subject to any disclaimer, the term of this patent is extended or adjusted under 35 U.S.C. 154(b) by 532 days.

(21) Appl. No.: 12/770,573

(22) Filed: Apr. 29, 2010

(65) Prior Publication Data

US 2010/0274280 A1 Oct. 28, 2010

Related U.S. Application Data

(63) Continuation of application No. PCT/US2008/082102, filed on Oct. 31, 2008.

(60) Provisional application No. 60/985,150, filed on Nov. 2, 2007.

(51) Int. Cl.
*A61B 17/08* (2006.01)
*A61F 2/92* (2013.01)
*A61B 17/00* (2006.01)
*A61B 17/22* (2006.01)

(52) U.S. Cl.
CPC ... *A61B 17/0057* (2013.01); *A61B 2017/00004* (2013.01); *A61B 2017/0065* (2013.01); *A61B 2017/00495* (2013.01); *A61B 2017/22047* (2013.01); *A61B 2017/00654* (2013.01); *A61F 2/92* (2013.01); *A61B 17/00491* (2013.01); *A61B 2017/00477* (2013.01)
USPC .......................................... 606/213

(58) Field of Classification Search
USPC ......... 606/157, 158, 191, 193, 194, 213, 214; 623/1.1, 1.44–1.48, 23.48, 23.58, 623/23.59, 23.64–23.67, 23.72, 23.75, 623/23.76; 424/422, 423
See application file for complete search history.

(56) References Cited

U.S. PATENT DOCUMENTS 2,115,492 A 4/1938 Kober
3,765,419 A 10/1973 Usher
(Continued)

FOREIGN PATENT DOCUMENTS

EP 0476178 A1 3/1992
EP 0482350 B1 4/1992
(Continued)

OTHER PUBLICATIONS

PCT International Search Report and Written Opinion for PCT/US2008/082102, Applicant: Incept, LLC, Forms PCT/ISA/220, PCT/ISA/210, and PCT/ISA/237: dated May 28, 2009, 13 pages.

*Primary Examiner* — Thomas McEvoy
(74) *Attorney, Agent, or Firm* — William A. English; Vista IP Law Group, LLP

(57) ABSTRACT

Apparatus and methods for sealing a puncture through tissue or otherwise treating a body lumen of a patient. The carrier includes at least one, but not all, of the adherent layer components required to form a tacky or sticky adherent layer on the carrier. The remaining adherent layer precursor(s) are delivered to the carrier in situ to form a sticky and/or tacky adherent layer on the carrier that enhances the attachment and retention of the carrier to tissue surrounding a target treatment location in which the carrier is delivered. The carrier may include hydrogel and/or other porous material, e.g., for releasing one or more agents carried by the carrier at the treatment location.

20 Claims, 12 Drawing Sheets

(56) References Cited

U.S. PATENT DOCUMENTS

| | | |
|---|---|---|
| 4,002,173 A | 1/1977 | Manning |
| 4,260,077 A | 4/1981 | Schroeder |
| 4,327,709 A | 5/1982 | Hanson et al. |
| 4,362,150 A | 12/1982 | Lombardi, Jr. et al. |
| 4,472,542 A | 9/1984 | Nambu |
| 4,540,404 A | 9/1985 | Wolvek |
| 4,655,211 A | 4/1987 | Sakamoto et al. |
| 4,664,857 A | 5/1987 | Nambu |
| 4,734,097 A | 3/1988 | Tanabe |
| 4,738,658 A | 4/1988 | Magro et al. |
| 4,838,280 A | 6/1989 | Haaga |
| 4,852,568 A | 8/1989 | Kensey |
| 4,890,612 A | 1/1990 | Kensey |
| 5,061,274 A | 10/1991 | Kensey |
| 5,104,375 A | 4/1992 | Wolf et al. |
| 5,104,389 A | 4/1992 | Deem et al. |
| 5,108,421 A | 4/1992 | Fowler |
| 5,192,300 A | 3/1993 | Fowler |
| 5,192,302 A | 3/1993 | Kensey et al. |
| 5,221,259 A | 6/1993 | Weldom et al. |
| 5,258,042 A | 11/1993 | Mehta |
| 5,259,835 A | 11/1993 | Clark et al. |
| 5,275,616 A | 1/1994 | Fowler |
| 5,290,310 A | 3/1994 | Makower et al. |
| 5,292,332 A | 3/1994 | Lee |
| 5,306,254 A | 4/1994 | Nash et al. |
| 5,320,639 A | 6/1994 | Rudnick |
| 5,324,306 A | 6/1994 | Makower et al. |
| 5,334,216 A | 8/1994 | Vidal |
| 5,383,896 A | 1/1995 | Gershony |
| RE34,866 E | 2/1995 | Kensey et al. |
| 5,391,183 A | 2/1995 | Janzen et al. |
| 5,409,703 A | 4/1995 | McAnalley |
| 5,413,571 A | 5/1995 | Katsaros et al. |
| 5,419,765 A | 5/1995 | Weldon et al. |
| 5,431,639 A | 7/1995 | Shaw |
| 5,437,292 A | 8/1995 | Kipshidze et al. |
| 5,437,631 A | 8/1995 | Janzen |
| 5,441,517 A | 8/1995 | Kensey et al. |
| 5,443,481 A | 8/1995 | Lee |
| 5,464,396 A | 11/1995 | Barta et al. |
| 5,486,195 A | 1/1996 | Myers et al. |
| 5,489,278 A | 2/1996 | Abrahamson |
| 5,514,158 A | 5/1996 | Kanesaka |
| 5,529,577 A | 6/1996 | Hammerslag |
| 5,550,187 A | 8/1996 | Rhee |
| 5,571,181 A | 11/1996 | Li |
| 5,580,923 A | 12/1996 | Yeung |
| 5,591,204 A | 1/1997 | Janzen et al. |
| 5,591,205 A | 1/1997 | Fowler |
| 5,601,602 A | 2/1997 | Fowler |
| 5,626,601 A | 5/1997 | Gershony et al. |
| 5,643,464 A | 7/1997 | Rhee |
| 5,660,849 A | 8/1997 | Polson et al. |
| 5,700,477 A | 12/1997 | Rosenthal |
| 5,716,375 A | 2/1998 | Fowler |
| 5,718,916 A | 2/1998 | Scherr |
| 5,725,498 A | 3/1998 | Janzen |
| 5,725,551 A | 3/1998 | Myers et al. |
| 5,728,122 A | 3/1998 | Leschinsky et al. |
| 5,731,368 A | 3/1998 | Stanley et al. |
| 5,741,223 A | 4/1998 | Janzen et al. |
| 5,744,153 A | 4/1998 | Yewey et al. |
| 5,752,974 A | 5/1998 | Rhee et al. |
| 5,780,044 A | 7/1998 | Yewey et al. |
| 5,782,860 A | 7/1998 | Epstein et al. |
| 5,785,679 A | 7/1998 | Abolfathi et al. |
| 5,795,331 A | 8/1998 | Cragg et al. |
| 5,830,130 A | 11/1998 | Janzen et al. |
| 5,836,970 A | 11/1998 | Pandit |
| 5,843,124 A | 12/1998 | Hammerslag |
| 5,916,236 A | 6/1999 | Muijs Van de Moer et al. |
| 5,922,009 A | 7/1999 | Epstein et al. |
| 5,928,266 A | 7/1999 | Kontos |
| 5,941,847 A | 8/1999 | Huber et al. |
| 5,948,429 A | 9/1999 | Bell |
| 5,948,829 A | 9/1999 | Wallajapet |
| 5,951,583 A | 9/1999 | Jensen et al. |
| 5,951,589 A | 9/1999 | Epstein et al. |
| 5,957,952 A | 9/1999 | Gershony |
| 5,972,375 A | 10/1999 | Truter |
| 5,973,014 A | 10/1999 | Funk |
| 6,017,359 A | 1/2000 | Gershony |
| 6,022,361 A | 2/2000 | Epstein et al. |
| 6,027,471 A | 2/2000 | Fallon et al. |
| 6,045,570 A | 4/2000 | Epstein et al. |
| 6,048,358 A | 4/2000 | Barak |
| 6,051,248 A | 4/2000 | Sawhney |
| 6,056,768 A | 5/2000 | Cates |
| 6,056,769 A | 5/2000 | Epstein et al. |
| 6,063,061 A | 5/2000 | Wallace |
| 6,083,522 A | 7/2000 | Chu |
| 6,093,388 A | 7/2000 | Ferguson |
| 6,123,723 A * | 9/2000 | Konya et al. ............ 623/1.11 |
| 6,152,943 A | 11/2000 | Sawhney |
| 6,162,240 A | 12/2000 | Cates et al. |
| 6,162,241 A | 12/2000 | Coury et al. |
| 6,165,201 A | 12/2000 | Sawhney |
| 6,179,862 B1 | 1/2001 | Sawhney |
| 6,238,412 B1 | 5/2001 | Dubrul et al. |
| 6,271,278 B1 | 8/2001 | Park |
| 6,287,323 B1 | 9/2001 | Hammerslag |
| 6,296,658 B1 | 10/2001 | Gershony |
| 6,299,597 B1 | 10/2001 | Buscemi et al. |
| 6,302,898 B1 | 10/2001 | Edwards et al. |
| 6,350,274 B1 | 2/2002 | Li |
| 6,368,300 B1 | 4/2002 | Fallon et al. |
| 6,371,975 B2 | 4/2002 | Cruise et al. |
| 6,379,373 B1 * | 4/2002 | Sawhney et al. ............ 606/193 |
| 6,458,147 B1 | 10/2002 | Cruise et al. |
| 6,475,177 B1 | 11/2002 | Suzuki |
| 6,514,534 B1 | 2/2003 | Sawhney |
| 6,562,059 B2 | 5/2003 | Edwards et al. |
| 6,566,406 B1 | 5/2003 | Pathak |
| 6,569,185 B2 | 5/2003 | Ungs |
| 6,605,294 B2 | 8/2003 | Sawhney |
| 6,608,117 B1 | 8/2003 | Gvozdic |
| 6,613,070 B2 | 9/2003 | Redmond et al. |
| 6,635,068 B1 | 10/2003 | Dubrul et al. |
| 6,689,148 B2 | 2/2004 | Sawhney |
| 6,699,261 B1 | 3/2004 | Cates et al. |
| 6,703,047 B2 | 3/2004 | Sawhney |
| 6,774,151 B2 | 8/2004 | Malmgren |
| 6,818,008 B1 | 11/2004 | Cates |
| 6,818,018 B1 | 11/2004 | Sawhney |
| 6,863,924 B2 | 3/2005 | Ranganathan |
| 6,887,974 B2 | 5/2005 | Pathak |
| 6,960,617 B2 | 11/2005 | Omidian |
| 7,790,192 B2 | 9/2010 | Khosravi et al. |
| 2001/0031948 A1 | 10/2001 | Cruise et al. |
| 2001/0046518 A1 | 11/2001 | Sawhney |
| 2001/0047187 A1 | 11/2001 | Milo et al. |
| 2001/0051813 A1 | 12/2001 | Hnojewyj |
| 2002/0015724 A1 | 2/2002 | Yang et al. |
| 2002/0062104 A1 | 5/2002 | Ashby et al. |
| 2002/0072767 A1 | 6/2002 | Zhu |
| 2002/0106409 A1 | 8/2002 | Sawhney et al. |
| 2002/0111392 A1 | 8/2002 | Cruise |
| 2002/0111651 A1 | 8/2002 | Ungs |
| 2002/0120228 A1 | 8/2002 | Maa et al. |
| 2002/0188319 A1 | 12/2002 | Morris et al. |
| 2003/0008831 A1 | 1/2003 | Yang et al. |
| 2003/0012734 A1 | 1/2003 | Pathak |
| 2003/0014075 A1 | 1/2003 | Rosenbluth et al. |
| 2003/0061735 A1 | 4/2003 | Todd et al. |
| 2003/0088269 A1 | 5/2003 | Ashby |
| 2003/0088271 A1 | 5/2003 | Cragg et al. |
| 2003/0100921 A1 | 5/2003 | Addis et al. |
| 2003/0135234 A1 | 7/2003 | Fisher et al. |
| 2003/0135236 A1 | 7/2003 | Fisher et al. |
| 2003/0139770 A1 | 7/2003 | Fisher et al. |
| 2003/0139771 A1 | 7/2003 | Fisher et al. |
| 2003/0139772 A1 | 7/2003 | Fisher et al. |
| 2003/0139773 A1 | 7/2003 | Fisher et al. |

(56) References Cited

U.S. PATENT DOCUMENTS

| | | |
|---|---|---|
| 2003/0233120 A1 | 12/2003 | Akerfeidt |
| 2004/0063206 A1 | 4/2004 | Rowley et al. |
| 2004/0093015 A1 | 5/2004 | Ogle |
| 2004/0121905 A1 | 6/2004 | Ranganathan et al. |
| 2004/0122350 A1 | 6/2004 | Zhong et al. |
| 2004/0147016 A1 | 7/2004 | Rowley |
| 2004/0230289 A1* | 11/2004 | DiMatteo et al. ............ 623/1.13 |
| 2004/0249342 A1 | 12/2004 | Khosravi |
| 2005/0027349 A1* | 2/2005 | Usiak et al. ................. 623/1.35 |
| 2005/0169882 A1 | 8/2005 | Lowe et al. |
| 2005/0267528 A1* | 12/2005 | Ginn et al. .................. 606/214 |
| 2006/0034930 A1 | 2/2006 | Khosravi |
| 2006/0079599 A1 | 4/2006 | Arthur |
| 2006/0099238 A1* | 5/2006 | Khosravi et al. ............ 424/423 |
| 2006/0100664 A1 | 5/2006 | Pai |
| 2007/0179600 A1* | 8/2007 | Vardi ........................... 623/1.44 |
| 2010/0274280 A1 | 10/2010 | Sawhney |
| 2010/0280546 A1 | 11/2010 | Campbell |

FOREIGN PATENT DOCUMENTS

| | | |
|---|---|---|
| WO | 9222252 | 12/1992 |
| WO | 9413210 A1 | 6/1994 |
| WO | 9922646 A1 | 5/1999 |
| WO | 0014155 | 3/2000 |
| WO | 0019912 | 4/2001 |
| WO | 03009764 A1 | 2/2003 |
| WO | 03087254 A2 | 10/2003 |
| WO | 03094749 | 11/2003 |

* cited by examiner

APPARATUS AND METHODS FOR SEALING A VASCULAR PUNCTURE

RELATED APPLICATION DATA

This application is a continuation of co-pending International Application No. PCT/US2008/082102 with an international filing date of Oct. 31, 2008, which claims priority to U.S. provisional application Ser. No. 60/985,150, filed Nov. 2, 2007, the entire disclosures of which are expressly incorporated by reference herein.

FIELD OF THE INVENTION

The present invention relates generally to apparatus and methods for sealing punctures in a body, e.g., a vascular puncture extending through tissue into a blood vessel, and to apparatus and methods for delivering a multiple component sealant into a puncture extending from a patient's skin to a blood vessel or other body lumen to seal the puncture.

BACKGROUND

Apparatus and methods are known for accessing a patient's vasculature percutaneously, e.g., to perform a procedure within the vasculature, and for sealing the puncture that results after completing the procedure. For example, a hollow needle may be inserted through a patient's skin and overlying tissue into a blood vessel. A guide wire may be passed through the needle lumen into the blood vessel, whereupon the needle may be removed. An introducer sheath may then be advanced over the guide wire into the vessel, e.g., in conjunction with or subsequent to one or more dilators.

A catheter or other device may be advanced through the introducer sheath and over the guide wire into a position for performing a medical procedure. Thus, the introducer sheath may facilitate accessing and/or introducing various devices into the vessel, while minimizing trauma to the vessel wall and/or minimizing blood loss. Upon completing the procedure, the device(s) and introducer sheath may be removed, leaving a puncture extending between the skin and the vessel wall.

To seal the puncture, external pressure may be applied to the overlying tissue, e.g., manually and/or using sandbags, until hemostasis occurs. This procedure, however, may be time consuming and expensive, requiring as much as an hour of a medical professional's time. It is also uncomfortable for the patient, and may require the patient to remain immobilized in the operating room, catheter lab, or holding area. In addition, a risk of hematoma exists from bleeding before hemostasis occurs.

Various apparatus and methods have been suggested for sealing a percutaneous puncture instead of using external pressure. For example, U.S. Pat. No. 5,108,421 to Fowler discloses a plug that may be delivered into a puncture through tissue. The plug is a cylindrical rod-shaped member which is constructed of a porous, bioabsorbable and expandable hemostatic collagen sponge or a polymerized polylactic acid or polyglycolic acid. In one embodiment, a catheter is inserted through the puncture into the blood vessel. A balloon on the catheter is expanded and retracted until the balloon is disposed adjacent the puncture at the wall of the vessel. The plug may be advanced into the puncture until the plug contacts the balloon. Once the plug is positioned within the puncture, the balloon may be deflated and withdrawn, leaving the plug within the puncture to expand and seal the puncture and/or to promote hemostasis.

U.S. Pat. Nos. 5,192,302 and 5,222,974 issued to Kensey et al. describe a bioabsorbable collagen plug that may be delivered through an introducer sheath into a puncture site.

U.S. Pat. No. 6,605,295 describes rods, plugs, crushed or irregularly shaped pieces of substantially dehydrated hydrogel that may be introduced into a lumen or void in a patient's body to seal or plug a biopsy needle track, reinforce weak tissue, or deliver a therapeutic compound. In one embodiment, a plug of dehydrated hydrogel may be deployed into the site of an arteriotomy and allowed to hydrate in the presence of the tissue fluids and blood, to fill the track of the catheter sheath and prevent further bleeding. By swelling to equilibrium hydration, the plug may lock itself firmly in place and thus reduce the risk of formation of a large hematoma at the site of the puncture.

U.S. Pat. No. 6,703,047 discloses dehydrated hydrogel precursor-based, tissue adherent compositions. The hydrogels may be used, for example, for sealing fluid leaks from tissue, as adherent drug delivery depots, and as means for augmenting and/or supporting tissue. The hydrogels may be administered directly to an open wound site or may be dispensed, e.g., using a non-adhesive backing material, an absorbable backing material, a syringe applicator, a powder atomization or aerosolization system, or a needle-less injector.

SUMMARY

The present invention is directed to apparatus and methods for sealing a puncture in a body, and, more particularly, to apparatus and methods for delivering a multiple component sealant into a percutaneous puncture. The sealant may include a carrier carrying one or more components, e.g., one or more sealant, adherent, and/or activating components that, when combined with one or more additional components, may create a sealant, e.g., a carrier with an adherent and/or sealing layer.

In accordance with one embodiment, a device is provided for sealing a puncture extending through tissue including a carrier having a predetermined shape, e.g., a disk, cylinder, rolled sheet or the like. The carrier includes one or more adherent components, e.g., one or more precursor(s) and/or activating agents, disposed thereon or contained therein, which may remain substantially unreactive until exposed to one or more additional adherent components. The remaining component(s), e.g., one or more additional precursors and/or activating agents, may be delivered to the carrier in situ to form a multiple component sealant. After delivering the additional component(s), a sticky or tacky adherent layer may form on the carrier, e.g., to enhance attachment and/or retention of the carrier to tissue surrounding the puncture, and/or to enhance hemostasis within the puncture.

In one embodiment, the adherent layer is made from "N" number of components, e.g., precursors and/or activating agents, wherein "N" is an integer of at least two (N≥2). The carrier is infused or otherwise loaded with "N−M" adherent layer precursors, wherein "M" is an integer from one and one less than "N" (1≤M≤(N−1)). According to this embodiment, the "M" number of sealant components may be delivered to the carrier in situ. For example, in an exemplary embodiment, the sealant may include three adherent components (N=3), e.g., two hydrogel or other polymer precursor components, and an activating component (such as a pH adjusting agent). Two of the components may be carried by the carrier before delivery, while the remaining component is delivered to the carrier in situ (N=3; M=1). Alternatively, one component may be carried by the carrier, and the remaining two adherent layer precursors are delivered to the carrier in situ (N=3; M=2).

In an exemplary embodiment, the carrier is infused with a solution including an amine-terminated polymer and an ester-terminated polymer. An aqueous solution including sodium borate is delivered to the carrier in situ. In another embodiment, the carrier is infused with a solution including an amine-terminated polymer and an aqueous solution including sodium borate. An aqueous solution including an ester-terminated polymer is delivered to the carrier in situ. In yet another embodiment, the carrier is infused with a solution including an ester-terminated polymer and an aqueous solution of sodium borate. An aqueous solution including an amine-terminated polymer is delivered to the carrier in situ.

In still another embodiment, the carrier is infused with a solution including an amine-terminated polymer. An aqueous solution including an ester-terminated polymer and sodium borate is delivered to the carrier in situ. In yet another embodiment, the carrier is infused with a solution including an ester-terminated polymer. An aqueous solution including an amine-terminated polymer and sodium borate is delivered to the carrier in situ. In yet another embodiment of the invention, the carrier is infused with a solution including sodium borate. A solution including an amine-terminated polymer and an ester-terminated polymer is delivered to the carrier in situ.

In accordance with another embodiment, a system is provided for sealing a puncture through tissue that includes a carrier carrying one or more components of a multiple component adherent material. The system also includes a source of one or more remaining components of the multiple component adherent material. The carrier may have the one or more components coated, infused, or otherwise applied to the carrier, e.g., in one or more external layers or embedded within the carrier material. The system may also include a sheath, catheter, or other cartridge that may carry the carrier for delivery into the puncture.

The source of the one or more remaining components may include one or more syringes or other cartridges containing the one or more remaining components in solid or liquid form. The source may be coupled to the cartridge used to deliver the carrier for infusing or otherwise delivering the one or more remaining components into the puncture.

Other aspects and features of the present invention will become apparent from consideration of the following description taken in conjunction with the accompanying drawings.

DETAILED DESCRIPTION OF THE EXEMPLARY EMBODIMENTS

Figure 1:
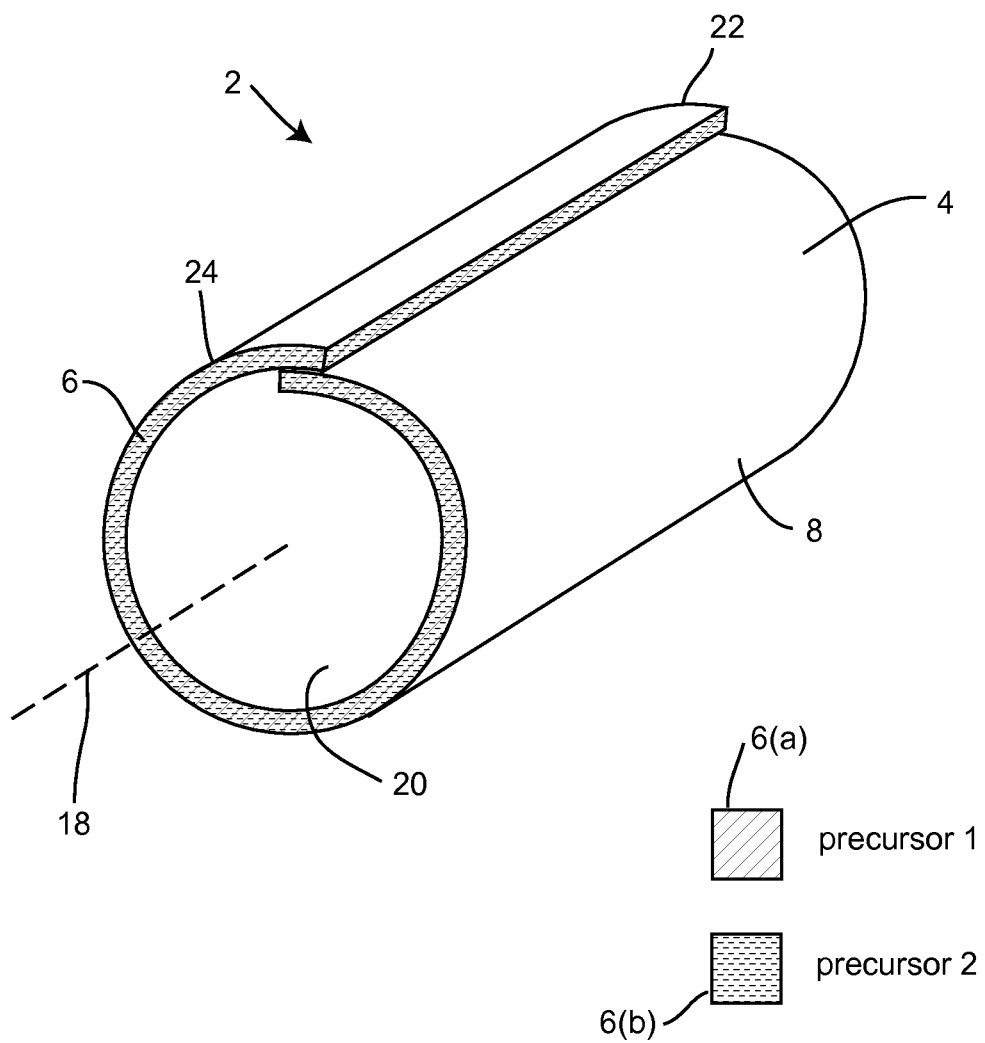
FIG. 1 is a perspective view of a carrier in the shape of a rolled sheet.

Turning to the drawings, FIG. 1 illustrates a device 2 for sealing a puncture extending through tissue (not shown). Generally, the device 2 includes a carrier or core 4 having carrying one or more adherent layer precursors 6 (FIG. 1 shows two such precursors 6(a), 6(b)). In one embodiment, the adherent layer precursors 6 may be infused or otherwise intermixed substantially throughout the carrier 4 (as shown in FIG. 1). In another embodiment, the adherent layer precursors 6 may be disposed on one or more exposed surfaces of the carrier 4, e.g., in one or more layers.

The carrier 4 includes some but not all of the adherent layer precursors 6 necessary to form an adherent layer (described in more detail below) on the carrier 4. One or more of the remaining adherent layer precursor(s) necessary to form the adherent layer on the carrier is/are delivered in situ, e.g., after the carrier 4 is disposed inside a puncture 90 extending through tissue 96 (not shown, see, e.g., FIGS. 5A-5D). For example, the remaining adherent layer precursor(s) may be located externally from the carrier 4. Thus, the adherent layer precursors and/or other components for creating an adherent and/or sealing layer on the carrier remain physically separated from one another until the time of application, i.e., after the carrier is delivered into the puncture 90, as explained further below.

This separation of two or more of the components of the device 2 has the unique advantage of increasing the shelf life of the device 2. By separating at least some of the adherent layer components from one another, the precursors 6 are prevented from at least partially reacting prematurely to form the tacky adherent layer. For example, if the carrier 4 contained all the necessary adherent layer precursors 6 before delivery, the precursors 6 may react at least partially with one another to form the tacky adherent layer even if the carrier 4 and adherent layer precursors 6 are in an otherwise neutral form. Thus, the tacky adherent layer of the device 2 may remain substantially unreactive for an extended period of time, and only begin formation after all of the adherent layer components are combined with one another.

In one embodiment, the carrier 4 is loaded with or otherwise includes "N−M" adherent layer precursor(s) 6, wherein "N" is an integer greater than one (N>1), and "M" is an integer from one to one less than "N" (1≤M≤(N−1)). In order for the tacky adherent layer to be produced, all "N" precursor components must be in physical contact with one another.

Thus, the tacky adherent layer may be produced by delivering the "M" adherent layer precursor(s) to the carrier 4 already including the "N–M" adherent layer precursor(s) 6. The "M" adherent layer precursor(s) 6 may be delivered in situ, wherein contact between "N" adherent layer precursors 6 produces an adherent layer on an exterior surface 8 of the carrier 4.

Table 1 below illustrates various configurations of the device for different numbers of adherent layer precursors 6 (two to four).

TABLE 1

| Number of precursors | N Value | M value | Number of precursors on carrier (N – M) | Number of precursors external to carrier (M) (e.g., delivered in situ) |
|---|---|---|---|---|
| 2 | 2 | 1 | 1 | 1 |
| 3 | 3 | 1 | 2 | 1 |
| 3 | 3 | 2 | 1 | 2 |
| 4 | 4 | 1 | 3 | 1 |
| 4 | 4 | 2 | 2 | 2 |
| 4 | 4 | 3 | 1 | 3 |

FIG. 1 illustrates a carrier 4 in the shape of a rolled sheet having a generally circular cross-sectional shape. It will be appreciated that the carrier 4 may have other cross-sections or shapes, such as elliptical, triangular, square, conical, disk, polygonic shapes, etc. The carrier 4 may be formed from a biocompatible and/or bioabsorbable material, for example, a porous, bioabsorbable foam or other solid material. In one embodiment, the carrier 4 may be formed from a biocompatible and/or bioabsorbable hydrogel, e.g., polyethylene glycol ("PEG"), or other synthetic material. In addition or alternatively, the carrier 4 may include pro-thrombotic material, e.g., including one or more biological pro-thrombotics, such as collagen, fibrin, carboxymethylcellulose, oxidized cellulose, alginates, gelatin, or other protein-based material, and/or synthetic materials, such as polyglycolic acids (PGA's), polyactides (PLA's), polyvinyl alcohol, and the like. The material of the carrier 4 may be at least partially absorbed by the body over time, e.g., over a period of days, weeks, or months. Optionally, the carrier 4 may include therapeutic and/or pharmaceutical agents, e.g., to promote healing, prevent infection and/or other adverse medical events, and the like. Such agents may be embedded in the carrier 4 material and/or applied as one or more coatings or layers. In addition, the material of the carrier 4 may have a substantially uniform composition or the composition may be varied, e.g., along its length and/or within underlying layers within the carrier 4.

In one embodiment, the carrier 4 is formed from a PEG-based hydrogel and the one or more adherent layer precursors 6 are infused into the hydrogel material of the carrier 4. For example, the hydrogel material of the carrier 4 may be formed and then placed into a solution including the one or more adherent layer precursors 6. The hydrogel material may be immersed in the desired loading solution (e.g., dissolved in deionized water ("DI $H_2O$")) and allowed to expand or swell until a steady-state condition (i.e., an equilibrium state) is reached. Generally, an equilibrium state may occur within about one to sixty (1-60) minutes after the hydrogel material contacts the loading solution. The hydrogel material is then removed from the loading solution and freeze dried (also sometimes referred to herein as "lyophilized"). For example, the hydrogel material may be freeze dried on a temperature controlled lyophilizer shelf at −50° C. or snap frozen in liquid nitrogen at −200° C.

Alternatively, the material forming the carrier 4 may be embedded or contacted with adherent layer precursors 6 by physically contacting the material of the carrier 4 with adherent layer precursors 6 in solid form (e.g., powder). The carrier 4 material may then be freeze dried and/or otherwise stored until subsequent use.

In one embodiment, the adherent layer precursors for the adherent layer may include at least two components, for example, a first electrophilic precursor and a second nucleophilic precursor, such that the two precursors may be reacted with each other to form a hydrogel. For example, each precursor may be a multi-armed PEG (e.g., with two to twelve (2-12) arms) with electrophilic or nucleophilic functional groups, such as an amine-terminated polymer and ester-terminated polymer. Optionally, the adherent layer may be formed from one or more additional components, such as a pH adjusting or other activating agent, e.g., sodium borate (e.g., $Na_2B_4O_7.10H_2O$). In this embodiment, one or two of the amine-terminated polymer, the ester-terminated polymer, and the sodium borate may be infused into a PEG-based hydrogel or other material of the carrier 4. For example, one or two of these components may be included in a loading solution, which may be applied to the carrier 4, as described above.

In one embodiment, the ester-terminated polymer may include a four arm, 10 kDalton PEG with reactive ester end groups. Alternatively, the ester-terminated polymer may include a four arm, 10 kDalton PEG with succinimidyl glutarate end groups or a four arm, 10 kDalton PEG with succinimidyl succinate end groups. As examples, the ester terminated polymer may include a four arm, 20 kDalton PEG with succinimidyl glutarate end groups or a four arm, 10 kDalton PEG with succinimidyl succinate end groups.

The amine-terminated polymer may include an eight arm, 20 kDalton PEG amine. The amine-terminated polymer may also include one or more small polypeptides with reactive amine groups, such as trilysine, a polypeptide made up of three lysine (Lys, K) amino acids. Other candidate amino acids for an amine-donating small polypeptide are arginine (Arg, R) and asparagine (Asn, N). These amine donating polypeptides may be made up of any of the 27 combinations of the three amino acids. Other precursors that may be included are disclosed in US Publication No. 2007/0231366 A1, published Oct. 4, 2007, the entire disclosure of which is expressly incorporated by reference herein. The adherent layer precursors 6 may be chosen based on their ability to rapidly swell (e.g., a 4 arm, 10 kDalton succinimidyl succinate combined with trilysine) or even their price, availability, and/or mechanical properties (e.g., a 4 arm, 20 kDalton succinimidyl glutarate combined with trilysine).

Figure 2A:
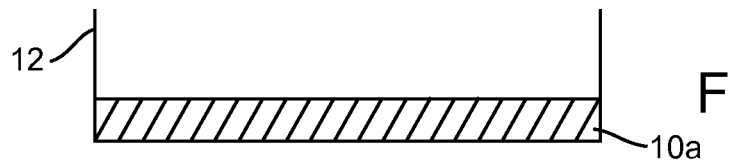
FIGS. 2A and 2B are side views of a mold for forming a laminate carrier structure from two or more hydrogel materials.
Figure 2B:
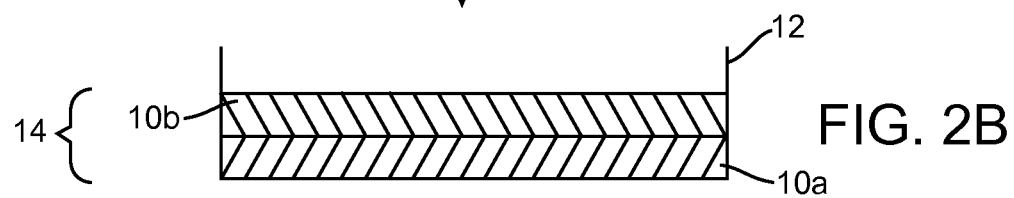

In one alternative embodiment, the carrier 4 may be formed from a composite or laminate structure including two or more layers of hydrogel material. The layers of hydrogel material may include individual or multiple components for the adherent layer. For example, with reference to FIGS. 2A and 2B, the carrier 4 may include multiple hydrogel layers 10, which may be formed by laminating, molding, or otherwise forming the multiple layers together. First, a hydrogel material for a first layer 10a may be poured or otherwise delivered into a mold 12. The hydrogel material may be poured into the mold in a liquid or fluid state such that it adopts the shape of or at least partially fills the mold 12. Before completing cross-linking of the hydrogel material (e.g., approximately 90% to completion), a second hydrogel material is poured over the first layer 10a to create a second layer 10b over the first layer 10a. The second layer 10b may slightly penetrate into the first hydrogel layer 10a, e.g., to enhance bonding or otherwise laminate the two layers 10a, 10b.

In one embodiment, the material forming the second layer 10b may be different from the material forming the first layer 10a. Optionally, a third or additional layers (not shown) may be applied over the second layer 10b. In this regard, multiple distinct hydrogel layers 10 may be created to form a laminate structure 14.

Before completing cross-linking of the second layer 10b (e.g., approximately 50% to completion), the mold 12 may be frozen and then freeze dried. Exemplary methods for freeze-drying are disclosed in US Publication No. 2007/0231366 A1, incorporated by reference above. The laminate 14 may then be removed from the mold 12 and shaped into a desired geometry for the carrier 4. For example, the laminate may be rolled into a cylindrical-shaped carrier 4 as is shown in FIG. 1. Alternatively, the laminate may be folded, cut, or otherwise formed into geometrical or other shapes, as desired.

Figure 3A:
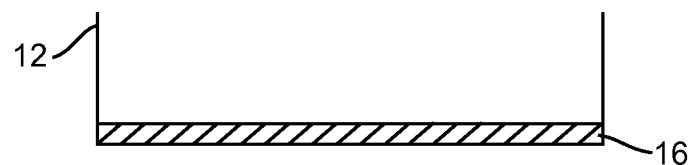
FIGS. 3A and 3B are side views of a mold for forming a carrier structure having an interpenetrating network of hydrogels.
Figure 3B:
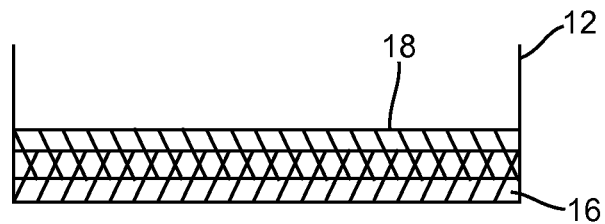

FIGS. 3A and 3B illustrate an alternative embodiment in which an interpenetrating network of hydrogels is formed. In contrast to the embodiment shown in FIGS. 2A and 2B, there is a significant amount of cross-linking between the multiple layers of hydrogel material. With reference to FIG. 3A, a freeze dried hydrogel material 16 may be fabricated and cut to fit into the bottom of the mold 12. Next, a solution 18 containing one or more of the adherent layer precursors 6 may be poured into the mold 12, thereby hydrating the lyophilized hydrogel material 16. The solution 18 may contain, for example, one or more of the following: an amine-terminated polymer, an ester-terminated polymer, and sodium borate. The adherent layer precursor solution 18 and the hydrogel material 16 may then be allowed to cross-link, e.g., for about 90 seconds. After cross-linking the materials, the mold 12 is then frozen, e.g., snap frozen in liquid Nitrogen, as described above. After freezing the mold, the materials in the mold 12 are then freeze dried. As seen in FIG. 3B, a two-layered freeze dried hydrogel is formed in which the two layers are interlinked with one another to a significant degree.

The multi-layer embodiments disclosed in FIGS. 2A, 2B, 3A, and 3B may be used to compose a carrier 4 in which the different layers have separate physical, chemical, or material properties. For example, one layer may provide a rapidly expanding hydrogel for arterial closure while a second layer could be physically tougher with a slower rate of expansion to facilitate tamping of the carrier 4 within a puncture 90.

In addition or alternatively, one or more of the layers described with respect to FIGS. 2A, 2B, 3A, and 3B may include one or more therapeutic and/or pharmaceutical agents. For example, one layer of a multi-layer structure may be loaded with an antibiotic material, a vasoconstrictor, a procoagulant or the like. In addition or alternatively, different components of the adherent layer may be provided in each of the layers of the laminate. For example, one layer may include one of the precursors, and another layer may include another of the precursors or an activating agent, similar to the methods described elsewhere herein.

In the embodiment shown in FIG. 1, the carrier 4 includes a lumen 20 extending between proximal 22 and distal ends 24, thereby defining a longitudinal axis 18. The lumen 10 may be created when the carrier 4 is formed, e.g., if the carrier 4 is rolled from one or more sheets or layers of material or formed by molding. Alternatively, the lumen 10 may formed by boring into or otherwise removing material from an already formed solid carrier 4. The lumen 10 is dimensioned such that a guide wire or other elongate member, such as a portion of a positioning member 60 (described in more detail below) may slide or otherwise pass through the carrier 4, e.g., while delivering the carrier 4 into the puncture 90.

Figure 4:
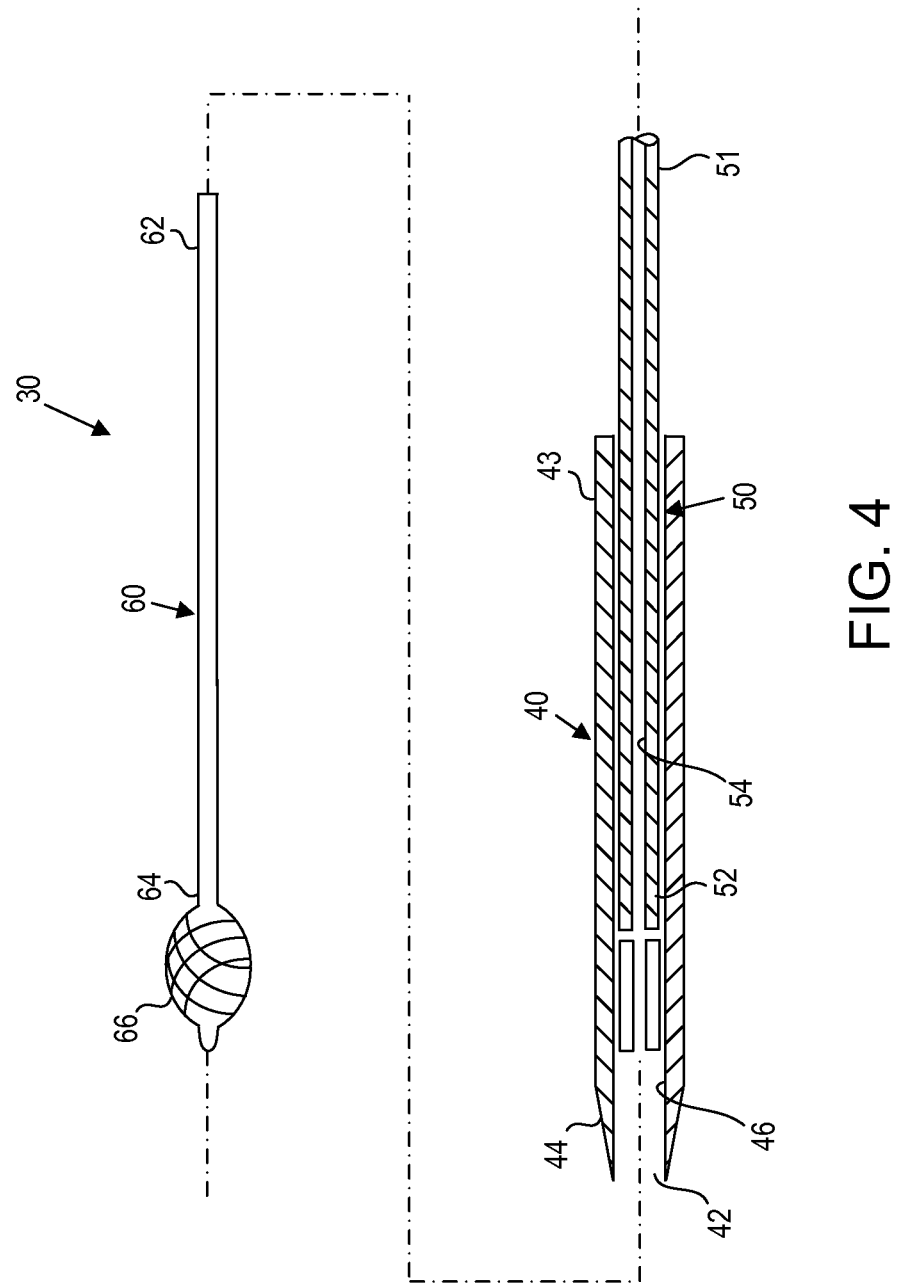
FIG. 4 is a cross-sectional side view of an apparatus for sealing a puncture extending through tissue.

Turning to FIG. 4, a delivery cartridge or apparatus 30 is shown for sealing a puncture 90 through tissue. Generally, the apparatus 30 may include a delivery sheath or other tubular member 40 having a lumen 42 sized to house a carrier 4, such as those described elsewhere herein. In addition, the apparatus 30 may include a plunger or other pusher member 50, and/or a positioning member 60. Additional information on a cartridge and methods for using it to deliver a carrier 4 may be found in co-pending application Ser. No. 10/982,384, the disclosure of which is expressly incorporated by reference herein.

The delivery sheath 40 may be a substantially rigid, semi-rigid, and/or flexible tubular body, including a proximal end 43, a distal end 44 having a size and shape for insertion into the puncture 90, and a lumen 42 extending therebetween. The distal end 44 may be tapered and/or may include a substantially atraumatic tip 46 to facilitate advancement through a puncture. The delivery sheath 40 may include a handle (not shown), and/or one or more seals, e.g., a hemostatic seal (also not shown), on the proximal end 43. The carrier device 4 may be disposed within the lumen 42 proximate to the distal end 44. The lumen 42 may be sized such that the carrier device 4 is slidable therein, e.g., able to traverse distally from the delivery sheath 40 during delivery, as described further below.

Figure 6:
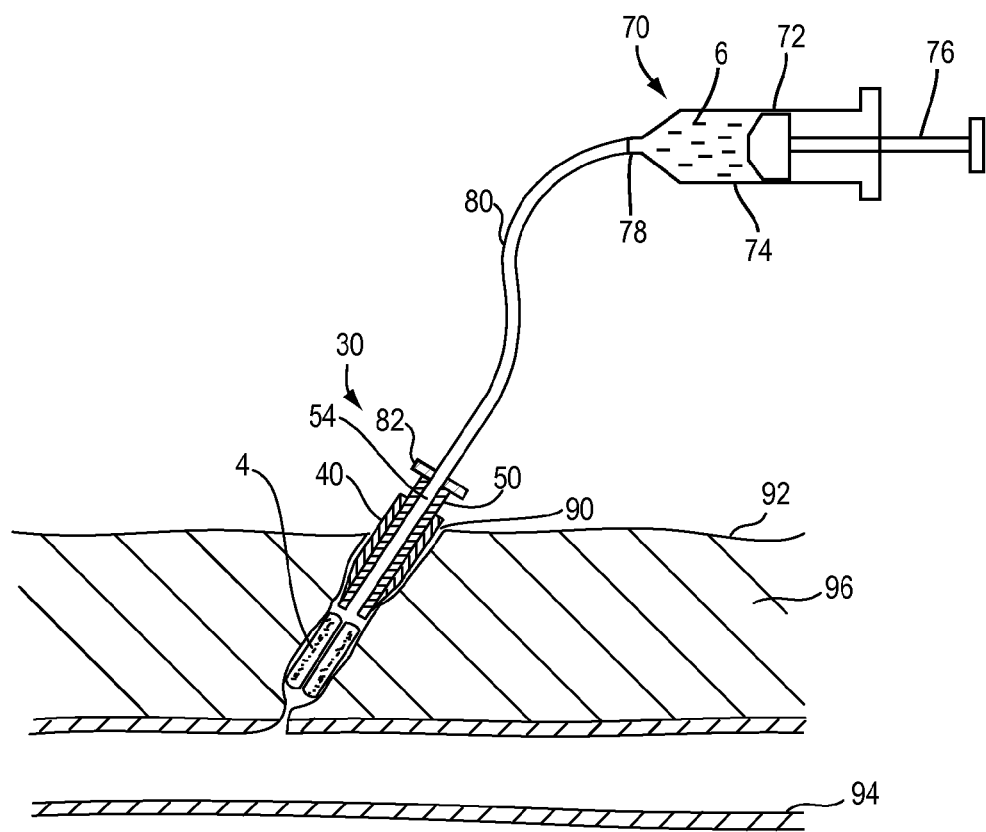
FIG. 6 is a cross-sectional view of a patient's body, showing an embodiment of a device for delivering one or more adherent layer precursors to a carrier in situ within a puncture.

The pusher member 50 may be an elongate member, e.g., a plunger, catheter, and the like, including a proximal end 51 and a distal end 52 having a size for slidable insertion into the lumen 42 of the delivery sheath 40. The proximal end 51 of the pusher member 50 may include a connector 82 (as best seen in FIG. 6) for coupling the lumen 54 of the pusher member 50 with a delivery device 70 (as seen in FIG. 6) for delivering the one or more additional adherent layer components to the carrier 4. Alternatively, a conduit 80, such as flexible tubing, may be directly inserted into the lumen 54 located at the proximal end 51 of the pusher member 50 for delivering the additional adherent layer component(s).

Still referring to FIG. 4, the distal end 52 of the pusher member 50 may be substantially blunt to facilitate contacting, tamping, pushing, and/or "cinching" the carrier device 4 within the delivery sheath 40 and/or puncture 90, as described further below. The pusher member 50 may be substantially rigid, semi-rigid, and/or substantially flexible, having sufficient column strength to allow movement of the delivery sheath 40 relative to the carrier device 4 without buckling the pusher member 50. In one embodiment, the pusher member 50 has sufficient column strength to tamp down the carrier 4 but retains a flexible or "floppy" distal end 52 to prevent accidental advancement of the carrier 4 into a vessel or other body lumen 94. The pusher member 50 may also include a lumen 54 extending between the proximal end 51 and the distal end 52, e.g., to accommodate the positioning member 60 and/or a guidewire (not shown).

In the embodiment shown in FIG. 4, the positioning member 60, e.g., a guidewire, and/or other solid or hollow elongate body, may include a proximal end 62, a distal end 64, and a positioning element 66 on the distal end 64. The positioning element 66 may be an expandable element, such as a wire mesh structure, as shown in FIG. 4, an expandable frame of the type shown in U.S. patent application Ser. No. 10/982, 384, the entirety of which is incorporated herein by reference, and/or an inflatable balloon (not shown). Optionally, the positioning element 66 may include a skin or other covering (not shown) on at least a proximal portion thereof, thereby making the positioning element 66 substantially nonporous.

The positioning element 66 may be biased to an enlarged condition, such as that shown in FIG. 4, but may be compressed to a contracted condition, e.g., by an overlying sleeve or other constraint (not shown). The constraint may be removed to expose the positioning element 66, allowing the positioning element 66 to automatically expand to the enlarged condition. Alternatively, the positioning element 66 may be selectively expandable, e.g., using a pullwire, source of inflation media, or other actuator (not shown) operable from the proximal end of the position member 60. For example, a syringe or other source of inflation media may be coupled to a lumen (not shown) extending through the positioning member 60 to an inflatable positioning element, such as those disclosed in FIGS. 8 and 9. Additional information on expandable structures that may be incorporated into positioning member 60 may be found in U.S. Pat. Nos. 6,238,412 and 6,635,068, in co-pending application Ser. No. 10/143,514, published as Publication No. US 2003/0078616 A1, and Ser. No. 10/454,362, filed Jun. 4, 2003, Ser. No. 10/806,927, filed Mar. 22, 2004, Ser. No. 10/928,744, filed Aug. 27, 2004, and Ser. No. 11/112,971, filed Apr. 22, 2005. The entire disclosures of these references are expressly incorporated herein by reference.

Turning to FIGS. 5A-5D, 6, and 7 exemplary methods are shown for sealing a puncture 90 using an apparatus, such as the cartridge 30 described above. Generally, the puncture 90 extends from a patient's skin 92 through intervening tissue 96, e.g., to a body lumen 94. In an exemplary embodiment, the puncture 90 may be a percutaneous puncture communicating with a blood vessel 94, such as a femoral artery, carotid artery, and the like.

In an exemplary method, the puncture 90 may be created using known procedures, e.g., using a needle, guidewire, one or more dilators, and the like (not shown). An introducer sheath (also not shown) may be advanced through the puncture 90 into the vessel 94, e.g., to provide access into the vessel 90 for one or more instruments, and/or allow one or more diagnostic and/or interventional procedures to be performed via the vessel 90, as is known in the art. Upon completing the procedure(s) via the vessel 94, any instruments and/or the introducer sheath (not shown) may be removed from the puncture 90.

Figure 5A:
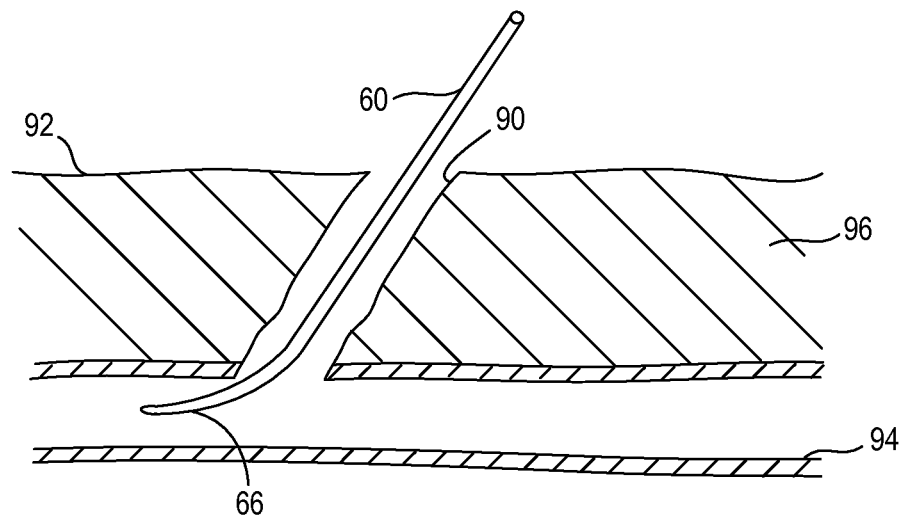
FIGS. 5A-5D are cross-sectional views of a patient's body, showing a method for sealing a puncture extending from the patient's skin through intervening tissue to a body lumen.
Figure 5B:
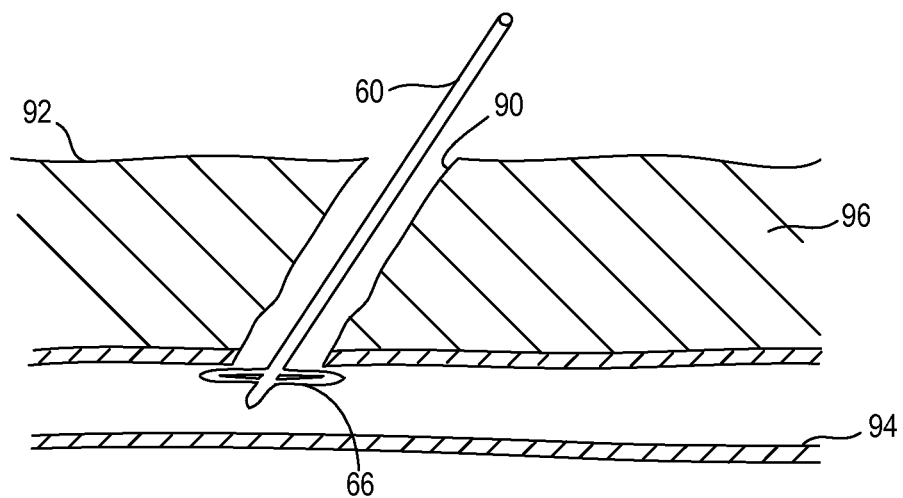

Turning to FIG. 5A, with the positioning element 66 collapsed, the positioning member 60 may be advanced through the puncture 90 until the positioning element 66 is disposed within the vessel 94, whereupon the positioning element 66 may be expanded to the enlarged condition shown in FIG. 5B. In one embodiment, the positioning member 60 may be advanced through the previously placed introducer sheath (not shown), e.g., before the introducer sheath is removed from the puncture 90. Alternatively, the positioning member 60 may be advanced directly through the puncture 90 after the introducer sheath is removed.

The positioning element 66 may be maintained in the contracted condition (shown in FIG. 5A) as it is advanced through the puncture 90, e.g., by an overlying sheath or other constraint (not shown). Once the positioning element 66 is disposed within the vessel 94, the constraint may be removed, allowing the positioning element 66 to expand automatically to the enlarged condition (shown in FIG. 5B). Alternatively, the positioning element 66 may be expanded to the enlarged condition via an actuator (not shown) on the proximal end 62 of the positioning member 60.

As shown in FIG. 5B, once the positioning element 66 is expanded, the positioning member 60 may be partially withdrawn from the puncture 90 until the positioning element 66 contacts the wall of the vessel 94, as shown in FIG. 5B. If the positioning element 66 is substantially nonporous, the positioning element 66 may substantially seal the puncture 90 from the vessel 94.

Figure 5C:
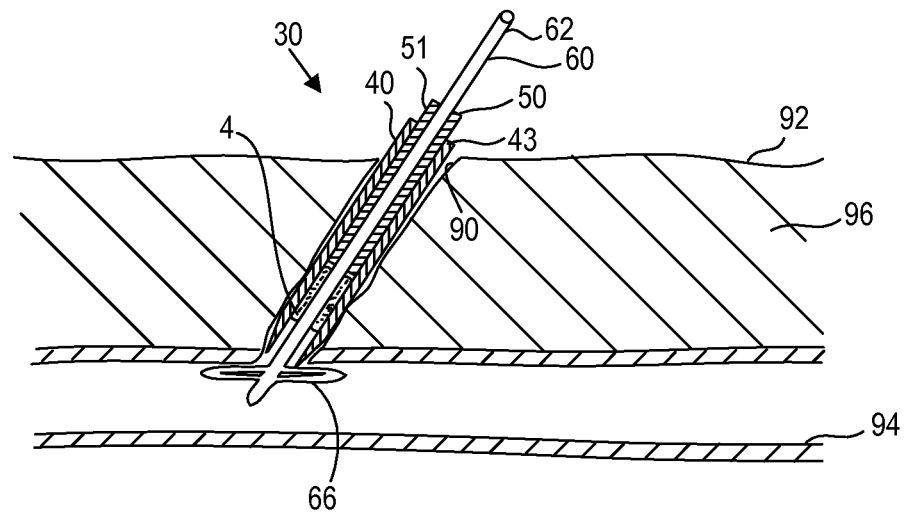

Turning to FIG. 5C, the cartridge 30 (carrying the carrier 4) may be introduced into the puncture 90, e.g., before or after the positioning element 66 is directed into contact with the wall of the vessel 94. For example, the cartridge 30 may be carried on a proximal end of the positioning member 60, i.e., remaining outside the puncture 90. The cartridge 30 may then be advanced over the positioning member 60, e.g., until the distal end 44 is disposed adjacent the vessel 94.

If the positioning element 66 has not yet been retracted, the proximal end 62 of the positioning member 60 may be pulled to draw the positioning element 66 against the distal end 44 of the delivery sheath 40 (providing a tactile feedback). The positioning member 60 may then be pulled further until the positioning element 66 contacts the wall of the vessel 94 (providing another tactile feedback), thereby partially in retracting the delivery sheath 40 back into the puncture 90.

Alternatively, if the positioning element 66 is already against the wall of the vessel 94, the delivery sheath 40 may be advanced until the distal end 44 contacts the positioning element 66 (or even vessel 94), thereby providing a tactile indication that the distal end 44, and consequently the carrier 4, are disposed adjacent the vessel 94. If the positioning element 66 substantially seals the puncture 90 from the vessel 94, this may prevent or minimize blood within the vessel 94 from entering the puncture 90, where it may seep into the lumen 42 of the delivery sheath 40 and contact the carrier 4.

Figure 5D:
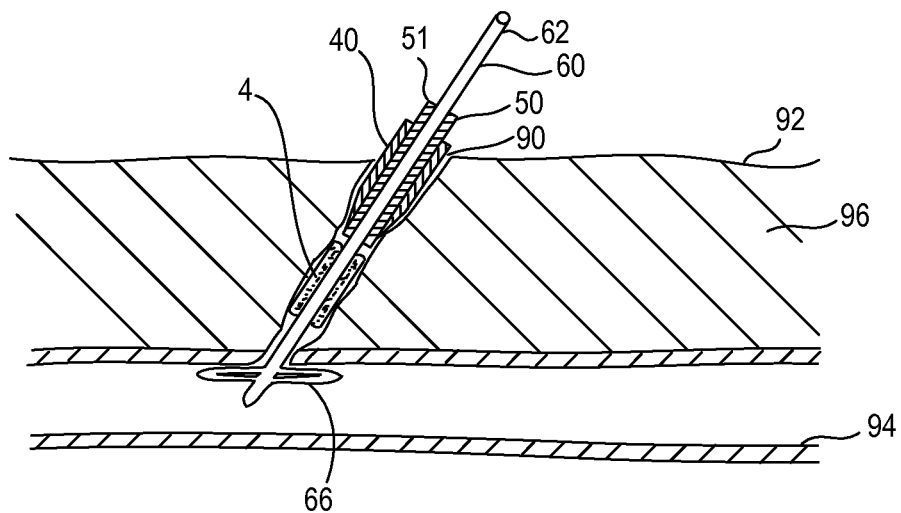

Turning now to FIG. 5D, the carrier 4 may then be deployed from the delivery sheath 40. For example, as described above with respect to FIG. 4, the cartridge 30 may include a pusher member 50 within the lumen 42 of the delivery sheath 40 and disposed proximal to the carrier 4. With the distal end 44 of the delivery sheath 40, and consequently the distal end 24 of the carrier 4, located proximal to the vessel 94, the delivery sheath 40 may be retracted proximally, while maintaining the pusher member 50 substantially stationary. Thus, the pusher member 50 may retain the carrier 4 in position within the puncture 90 while the delivery sheath 40 is retracted from around the carrier 4.

In one embodiment, the carrier 4 may be offset proximally from the distal end 44 of the delivery sheath 40 a predetermined distance, e.g., between about two millimeters and ten millimeters (2-10 mm), such that the carrier 4 is delivered within the puncture 90 offset proximally from the vessel 94. Alternatively, the carrier 4 may be located immediately adjacent the distal end 44 of the delivery sheath 40.

Alternatively, the pusher member 50 may be advanced distally relative to the delivery sheath 40 to deliver the carrier 4 into the puncture 90. For example, the pusher member 50 may be advanced until the carrier 4 abuts the positioning element 66 of the positioning member 60, e.g., before or after retracting the delivery sheath 40. Alternatively, the pusher member 50 may be advanced until the carrier 4 abuts a wall of the vessel 94. This may ensure that the carrier 4 is delivered adjacent to the vessel 94, providing tactile feedback when the carrier 4 abuts the positioning element 66 or wall of the vessel 94.

As shown in FIG. 5D, if desired, the pusher member 50 may be used to tamp, compress, pack, or cinch the carrier 4 within the puncture 90. For example, after the carrier 4 is exposed within the puncture 90 (e.g., using one of the methods described above), the pusher member 50 may be advanced to push the carrier 4 distally against the positioning element 66 or vessel wall 94. This may place the distal end 24 of the carrier 4 adjacent to or against the wall of the vessel 94, which may enhance hemostasis in the arteriotomy between the vessel 94 and the puncture 90. Optionally, the pusher member 50 may be advanced further, thereby compressing the carrier 4 axially, which may enhance the carrier 4 expanding radially to fill the puncture 90 and/or permeate outwardly against or into the surrounding tissue.

Once the carrier 4 is positioned within the puncture 90, the one or more additional adherent layer components may be delivered into the puncture 90 to the carrier 4. As seen in FIG. 6, the additional component(s) may be delivered via a delivery device 70, such as a syringe 72 that includes a barrel 74 carrying the additional component(s). The syringe 72 includes a plunger 76 for dispensing the additional component(s) from the barrel 74, e.g., through outlet 78, which may be coupled to a conduit, such as flexible tubing 80. Optionally, the delivery device may include two or more separate chambers (not shown) including one or more of the additional component(s). The components in the chambers may be mixed together, e.g., as fluid passes from a first chamber into a second chamber, etc., until the mixed fluid, carrying the components passes through tubing 80 into the puncture 90.

The tubing 80 may be connected to a nipple or other connector 82 located on the proximal end 51 of pusher member 50 (or, alternatively, directly to the proximal end 51 of the pusher member 50). Optionally, the connector 82 may include a Luer lock connector 82 and the like to enable the tubing 80 to be quickly connected and/or disconnected. Alternatively, the lumen 54 of the pusher member 50 may be sized to receive and retain the conduit 80 in an interference fit or similar arrangement.

One or more additional adherent layer components may then be delivered to the carrier 4 in situ, e.g., by depressing the plunger 76 of the syringe 72. The additional component(s) may flow through the lumen 54 directly onto the carrier 4 located in the puncture 90. The additional component(s) may migrate or otherwise flow around the external surface of the carrier 4 and/or within the lumen 20 of the carrier 4. Optionally, the additional component(s) may permeate into material of the carrier 4, e.g., into one or more layers thereof, for mixing the additional component(s) with the components already carried by the carrier 4.

As the additional component(s) mix with or contact the components carried by the carrier 4, they may begin to react to form an adherent layer 5 (seen in FIG. 11) around the carrier 4. For example, the components may mix to create a sticky or tacky coating of hydrogel around the carrier 4, which may bond or otherwise adhere to tissue surrounding the carrier 4. Optionally, if one or more of the components carried by the carrier 4 are in solid form, e.g., embedded or dried within the carrier 4, the fluid conveying the additional component(s) to the carrier 4 may dissolve such component(s) to facilitate the initiation of the reaction to create the adherent layer 5.

Figure 7:
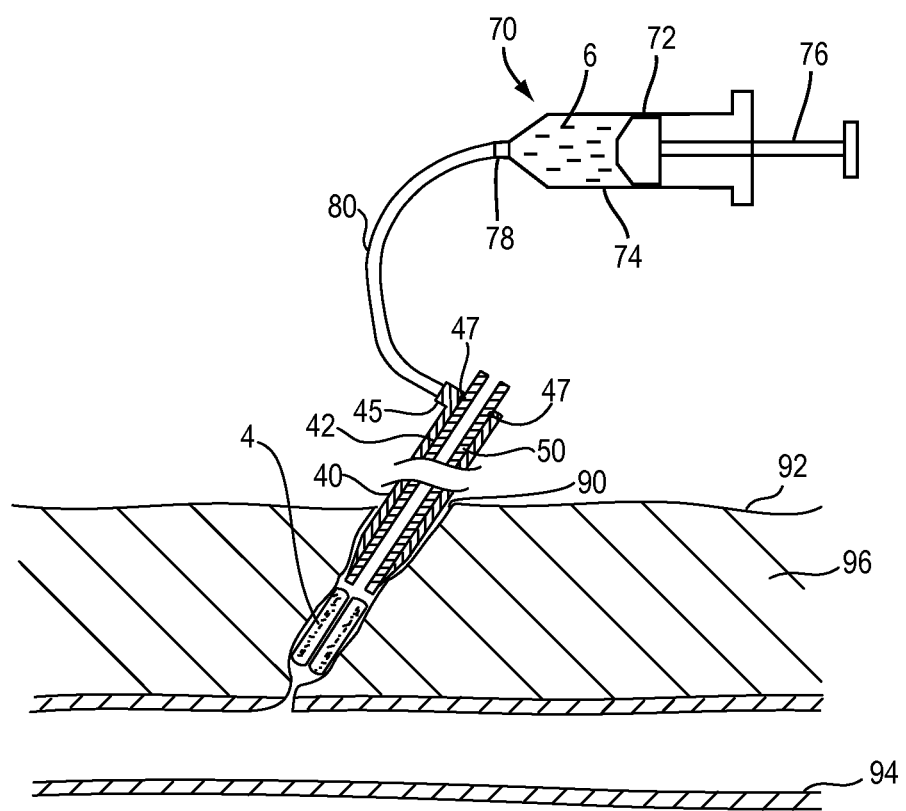
FIG. 7 is a cross-sectional view of a patient's body, showing another embodiment of a device for delivering one or more adherent layer precursors to a carrier in situ.

In an alternative embodiment, as shown in FIG. 7, the syringe 72 may be coupled to the lumen 42 of the delivery sheath 40 via tubing 80. For example, the tubing 80 may be connected at one end to the syringe 72 and at the other end to a side port 45 on the delivery sheath 40 that communicates with the sheath lumen 42. In this embodiment, an o-ring or other seal 47 may be provided between the pusher member 50 and the delivery sheath 40, e.g., to prevent the additional component(s) from leaking out the proximal end of the apparatus 30.

While FIGS. 6 and 7 omit the positioning member 60, it will be appreciated that the additional component(s) may be delivered into the puncture 90 and/or to the carrier 4 with or without the positioning member 60 remaining within the puncture 90. For example, in one embodiment, the positioning element 66 may be collapsed and the positioning member 60 removed before delivering the additional component(s). In this embodiment, some of the fluid carrying the additional component(s) may escape from the puncture 90 into the body lumen 94. Because hydrogel precursors may remain substantially inert, bodily fluids may carry this fluid away, where the additional component(s) may be metabolized by the body.

Alternatively, the additional component(s) may be delivered in situ to the carrier 4 with the positioning member 60 remaining within the puncture 90, i.e., extending through the lumen of the carrier 4, as shown, for example, in FIG. 5D. In this case, the one or more additional components may be delivered via the sheath lumen 42 of the delivery sheath 40 (as shown in FIG. 7) or the via the lumen 54 of the pusher member 50 (between the outer surface of the positioning member 60 and the interior surface of pushing member lumen 54). The pusher member 50 or delivery sheath 40 may include a side port through which the additional component(s) may be delivered without interfering with the positioning member 60.

Figure 8:
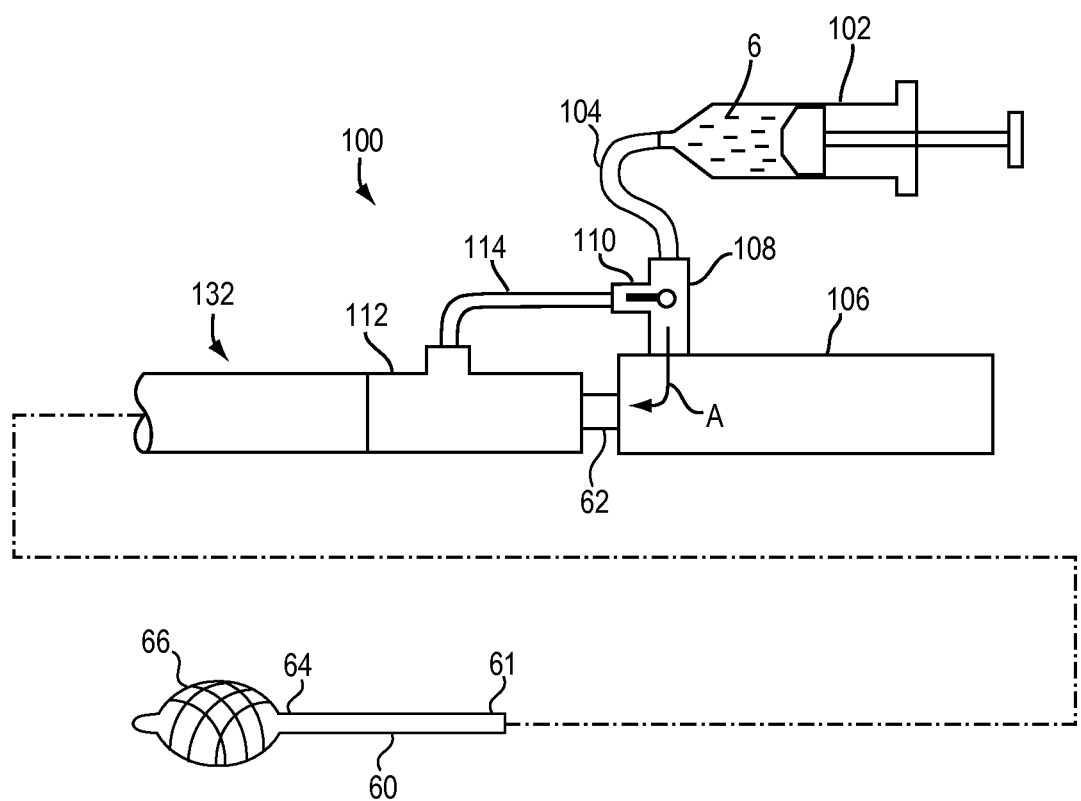
FIG. 8 is a cross-sectional side view of another embodiment of a device for delivering one or more adherent layer precursors to a carrier in situ.

FIG. 8 illustrates an alternative embodiment of an apparatus 100 for sealing a puncture through tissue. The apparatus 100 generally includes a positioning member 60, i.e., a tubular member 61 carrying a balloon or other expandable positioning element 66 on a distal end 64 thereof. The positioning member 60 includes a hub 106 on its proximal end that has an interior communicating with an interior of the positioning element 66 via a lumen in the tubular member 61. In addition, the apparatus 100 includes a cartridge 132, which may include an outer sheath 140, an inner pusher member (not shown), and a carrier with one or more adherent layer components (also not shown), similar to other embodiments described elsewhere herein. The apparatus 100 also includes a valve assembly 108 that may be alternately coupled to the hub 106 and a lumen of the cartridge 132, as explained further below.

In this embodiment, fluid carrying one or more additional adhesive layer components may be used both to inflate the balloon 66 and to bathe the carrier with the additional component(s), e.g., to create an adhesive layer around the carrier 4, as described elsewhere herein. Thus, separate syringes may not be needed to expand the balloon 66 and deliver the additional component(s) to the carrier. As shown in FIG. 8, a syringe 102 having one or more adhesive layer components 6 therein is coupled to a conduit 104, which is connected, in turn, to the valve assembly 108. The valve assembly 108 may include a valve 110, such as a stopcock or other manual or motorized valve, that may selectively direct the flow of the additional component(s) along two paths.

For example, when the valve 110 is in a first position, shown in FIG. 8, the additional component(s) 6 may flow into the hub 106, and consequently, through the tubular member 61 into the balloon 66. Thus, the syringe 102 may be used to deliver or evacuate fluid from the balloon 66 to expand or collapse the balloon 60. For example, with the balloon 66 collapsed, the tubular member 61 may be advanced into a puncture through tissue, e.g., until the balloon 66 is located within a body lumen. The balloon 66 may then be expanded, and partially retracted to seal and/or substantially isolate the body lumen from the puncture, similar to the embodiments described elsewhere herein.

Figure 9:
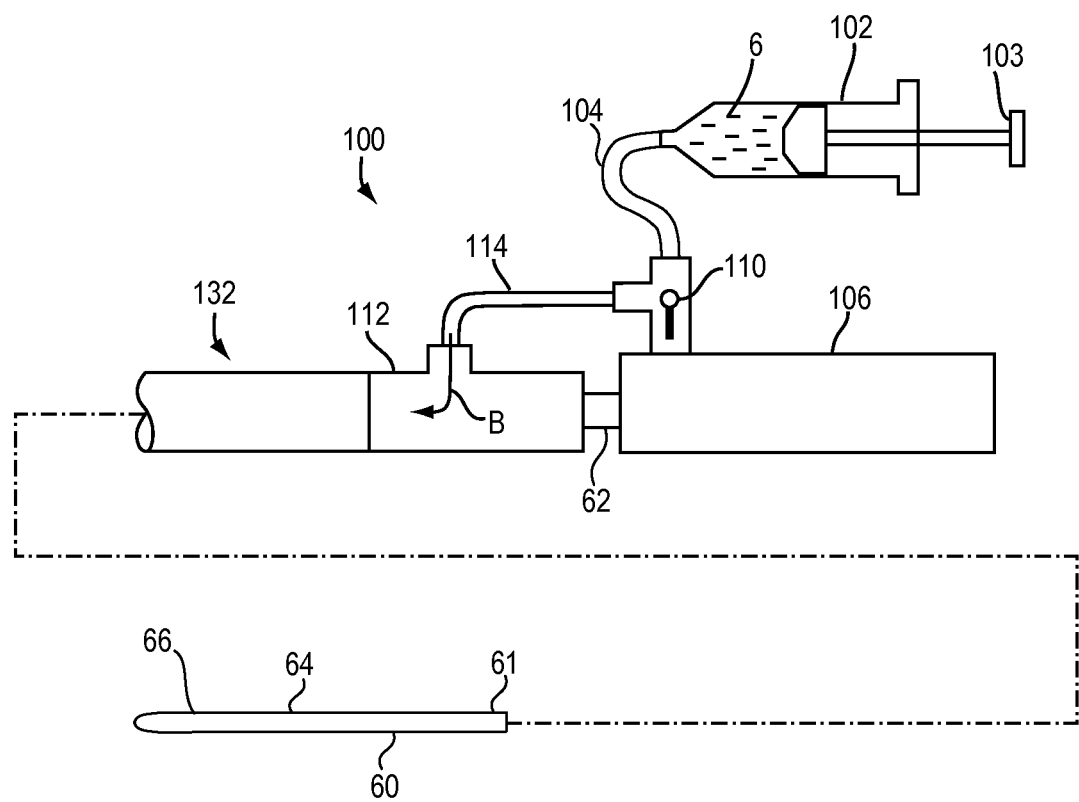
FIG. 9 is a cross-sectional side view of yet another embodiment of a device for delivering one or more adherent layer precursors to a carrier in situ.

Turning to FIG. 9, the valve 110 may be turned to a second position, e.g., in which the syringe 102 communicates with tubing 114, which is coupled to a hub 112 on the cartridge 132. Thus, in the second position, the additional component(s) may be delivered into the cartridge 132 (as represented by arrow "B"), and, consequently, through the puncture to the carrier, similar to other embodiments described herein. In this embodiment, the tubing 114 may be substantially flexible or otherwise may allow the cartridge hub 112 to move axially relative to the hub 106 on the positioning member 60. For example, the cartridge hub 112 may be coupled to an outer sheath on the cartridge 132, allowing the outer sheath to be retracted to expose the carrier within a puncture, similar to the methods described elsewhere herein.

Generally, before the valve 110 is moved to the second position, fluid may be evacuated from the balloon 66 back into the syringe 102 to collapse the balloon 66 for removal. Thereafter, when the plunger 103 of the syringe 102 is depressed, the additional component(s) 6 bypass the hub 106 and pass via the lumen inside the cartridge 132 directly onto and/or around the carrier 4, thereby initiating the formation of the sticky or tacky adherent layer 5 on the carrier 4, as described elsewhere herein. Some of the additional component(s) may flow past the carrier, e.g., into the body lumen, where the additional component(s) may be carried away by bodily fluids.

Alternatively, the balloon 66 may remain inflated, e.g., to seal the body lumen from the puncture, while the additional component(s) are delivered to the carrier. In this alternative, the valve 110 may be returned to the first position to allow the balloon 66 to be collapsed before removing the positioning member 60 after the additional component(s) are delivered to the carrier.

Figure 10A:
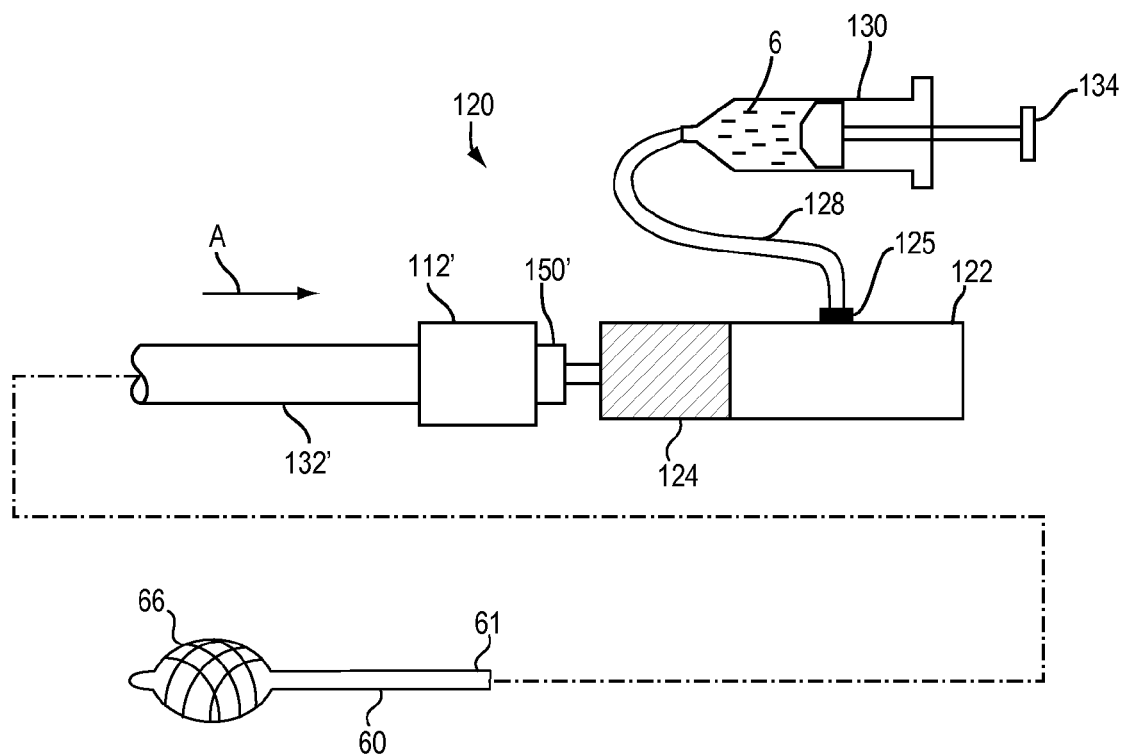
FIGS. 10A and 10B are cross-sectional side views of another embodiment of a device for delivering one or more adherent layer precursors to a carrier in situ, showing a cartridge unretracted and retracted, respectively to engage a check valve on a hub of the device.
Figure 10B:
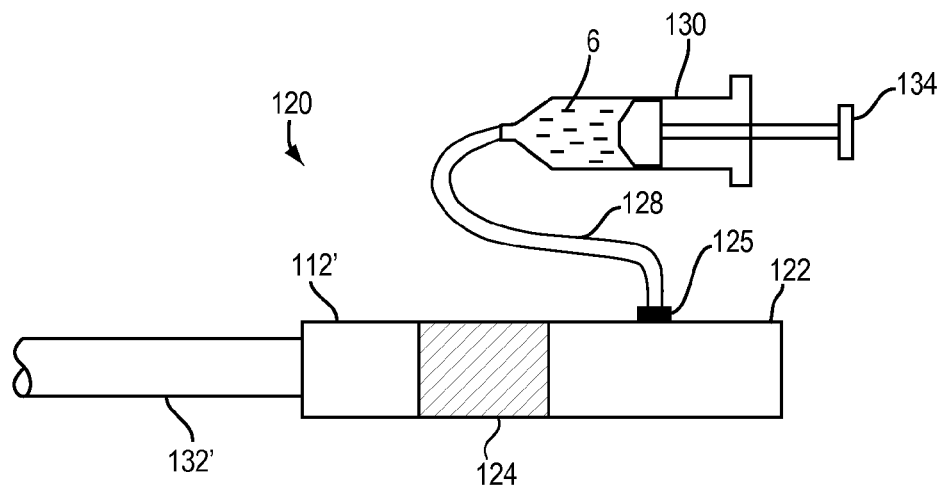

Turning to FIGS. 10A and 10B, another embodiment of an apparatus 120 is shown that may be used for delivering fluid including one or more additional adherent layer components 6 both to expand balloon 66 and deliver the one or more adherent layer components 6 to a carrier (not shown). Similar to the previous embodiment, the apparatus 120 includes a hub 122 having an interior (not shown) coupled to a check valve 124, such as a duck bill valve or other one-way valve. The interior of the hub 122 communicates with a port 125 on the hub 126 that may be connected via a conduit, such as tubing 128, to a source of the additional component(s), such as a syringe 130, similar to the previous embodiments.

With particular reference to FIG. 10A, the positioning member 60 includes a tubular member 61 including a lumen therein (not shown) that communicates between the hub 126 and an interior of the balloon 66. A cartridge 132' is provided around the tubular member 61 that includes a hub 112' and a nipple 150' or other connector extending proximally therefrom. The hub 112' may be slidable axially, i.e., proximally, relative to the tubular member 61, e.g., such that the nipple 150' may be engaged with the check valve 124, as shown in FIG. 10B. Once connected in this manner, the check valve 124 may be opened, permitting fluid from the syringe 130 (i.e., carrying the additional adherent layer component(s) 6) to pass through the hub 122 into the cartridge hub 122. Consequently, the fluid may be carried via the outer sheath or pusher member (not shown) of the cartridge 132' to the carrier, similar to the previous embodiments.

During use, the apparatus 120 may be provided as shown in FIG. 10A. In this position, the lumen of the tubular member 61 communicates with the interior of the hub 122. Thus, when the plunger 134 of the syringe 130 is depressed, the additional adherent layer component(s) 6 may pass from the syringe 130, through the tubing 128, interior of the hub 122, lumen of the tubular member 61, and into the balloon 66 to expand the balloon 66 to an enlarged condition, as shown in FIG. 10A. In this position, the nipple 150', and consequently the cartridge 132 does not communication with the interior of the hub 122.

The carrier (not shown) carried by the cartridge 132 may then be deployed within a puncture, e.g., similar to the methods described above. After the carrier is deployed within the puncture 90, the balloon 66 is collapsed, e.g., by pulling the plunger 134 of the syringe 130. The positioning member 60 may then be retracted proximally (represented by arrow A in FIG. 10A) such that the collapsed balloon 66 is retracted through the carrier, e.g., into the pusher member or outer sheath of the cartridge 132'.

The cartridge hub 112' may then be retracted proximally until the nipple 150' engages the check valve 124. The nipple 150' may open the check valve 124 such that the interior of the hub 122 communicates with one or more lumens within the cartridge 132', e.g., the lumen of the pusher member. The plunger 134 of the syringe 130 may then be depressed to deliver the one or more additional adherent layer components to the carrier, e.g., via the lumen of the pusher member. The additional component(s) may then bathe or otherwise contact the carrier disposed in the puncture 90 to create the adherent layer, as described elsewhere.

In this embodiment, as the additional component(s) 6 are delivered to the carrier in situ, the additional component(s) 6 may also flow through the tubular member 61 into the balloon 66. Because the balloon 66 is retracted into the pusher member or outer sheath, the balloon 66 may not expand, allowing the balloon 66 to be removed from the puncture, e.g., when the apparatus 120 is removed. Alternatively, when the nipple 150' engages the check valve 124, this may activate a seal within the hub 122 that substantially isolates the lumen of the tubular member 61 from the hub 122. Thus, when the additional component(s) are delivered to the carrier, none of the fluid may pass through the tubular member 61 into the balloon 66.

In the delivery device shown in FIGS. 8, 9, 10A, and 10B, a single device may be used both to deploy the positioning element 66 and to deliver one or more adherent layer components 6 to the carrier 4 in situ. In this embodiment, the one or more adherent layer components 6 may be a substantially incompressible liquid capable both of inflating the positioning element 66 and dissolving or otherwise carrying the additional component(s) to the carrier to create the adherent layer. Thus, the additional component(s) and/or fluid carrying the additional component(s) should remain inert or otherwise not react with the material of the balloon 66 or other components of the apparatus 120, e.g., that may otherwise prevent the balloon 66 from being collapsed before removal from the puncture.

Optionally, after the carrier is deployed within the puncture (using any of the apparatus and methods described herein), additional sealing compounds may be delivered into the puncture, e.g., to fill all or a portion of the puncture above and/or around the carrier. For example, with reference to FIG. 4, the delivery sheath 40 or pusher member 50 may be used to deliver liquid sealing compound, e.g., hydrogel precursors (not shown), into a puncture, e.g., through the lumen 42 of the delivery sheath 40 or lumen 54 of the pusher member 50, or through a separate lumen (not shown) in either device.

In one embodiment, the delivery sheath 40 may include one or more side ports (not shown) on the proximal end of the delivery sheath 40 that may be coupled to a source of sealing compound, such as a syringe assembly storing hydrogel precursors (not shown). If the delivery sheath 40 has not been removed entirely from the puncture, the delivery sheath 40 may be advanced into the puncture until the distal end 44 is disposed adjacent the carrier 4, whereupon the sealing compound may be delivered into the puncture.

Alternatively, the delivery sheath 40 may be retracted as the sealing compound is delivered, e.g., to at least partially fill the puncture. In a further alternative, e.g., if the delivery sheath 40 has been removed, the pusher member 50 may be used to deliver sealing compound in a similar manner to those just described. In still another alternative, a separate sheath or other delivery device (not shown) may be introduced into the puncture to deliver the liquid sealing compound above and/or around the carrier 4. Exemplary apparatus and methods for delivering such sealing compounds into the puncture are disclosed in co-pending application Ser. No. 10/454,362, filed Jun. 6, 2003, and Ser. No. 10/806,952, filed Mar. 22, 2004, the entire disclosures of which are expressly incorporated by reference herein.

Figure 11:
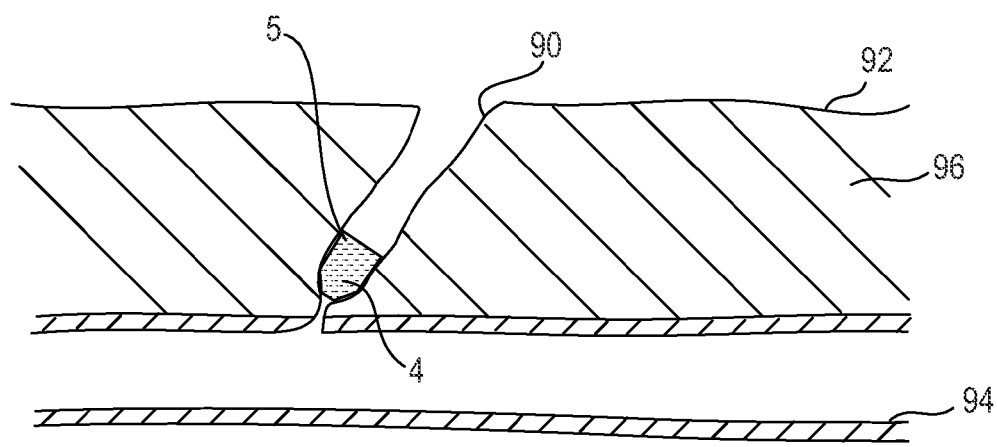
FIG. 11 is a cross-sectional view of a patient's body, showing a carrier delivered within a puncture extending from the patient's skin through intervening tissue to a body lumen.

Turning to FIG. 11, any of the apparatus described herein, e.g., such as the positioning member 60, pusher member 50, and/or delivery sheath 40 of FIG. 4 may then be removed, leaving the carrier 4 within the puncture 90. The components of the apparatus 30 may be removed in any desired order. For example, in one method, the positioning member 60 may be withdrawn through the carrier 4 and the lumen 54 of the pusher member 50. The pusher member 50 may restrain the carrier 4 from moving proximally as the positioning member 60 is removed. Once the positioning member 60 is removed, the pusher member 50 (and the delivery sheath 40, if not already removed) may then be removed.

Alternatively, the delivery sheath 40 and pusher member 50 may be withdrawn first followed by the positioning member 60. If the positioning member 60 is removed, the positioning element 66 may be collapsed to allow the positioning member 60 to be removed through the lumen 20 of the carrier 4 without substantially moving or disrupting the carrier 4. For example, a sleeve or other constraint (not shown) may be advanced over the positioning member 60 until it contacts and forces the positioning element 66 to collapse as it enters the sleeve. Alternatively, if the positioning element 66 is controlled by an actuator (not shown), the actuator may be manipulated to collapse the positioning element 66 before the positioning member 60 is removed. In another alternative, the positioning member 60 may simply be pulled proximally until the positioning element 66 contacts the carrier 4 and forces the positioning element 66 to collapse as it enters the lumen 20 of the carrier 4.

With the positioning element 66 collapsed, blood and/or other fluid within the vessel 94 may enter the puncture 90, thereby exposing the carrier 4 to an aqueous physiological environment. The aqueous physiological environment, which may include blood or other bodily fluids from the vessel 94 (or other body lumen) may wet the carrier 4 and assist in promoting the mixing and/or reaction of the adherent layer precursors 6. The reaction of the adhesive layer precursors 6 forms an adhesive or "sticky" layer 5 that may bond or otherwise attach to tissue surrounding the puncture 90, which may facilitate retaining the carrier 4 in place within the puncture 90. In addition, the adherent layer 5 may also expand or swell to further aid in retaining the carrier 4 within the puncture 90 and/or enhance sealing the puncture 90.

Optionally, if the carrier 4 includes pro-thrombotic material, the material may cause and/or accelerate coagulation of the blood within the puncture 90, thereby enhancing hemostasis. Optionally, as the carrier 4 contacts blood, the carrier 4 may expand to substantially occlude the lumen 20, although alternatively, the lumen 20 may be sufficiently small to seal by natural hemostasis of the blood. In addition, if the carrier 4 includes therapeutic and/or pharmaceutical agent(s), the blood and/or surrounding tissue may become exposed to the agent(s), thereby enhancing hemostasis, patient comfort, healing, and the like.

Figure 12A:
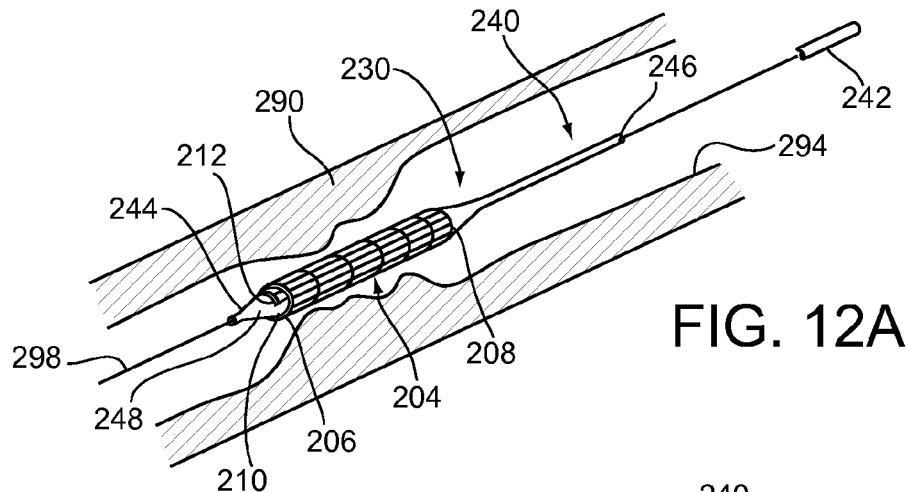
FIGS. 12A-12C are cross-sectional perspective views of a blood vessel being lined by a hydrogel structure.
Figure 12B:
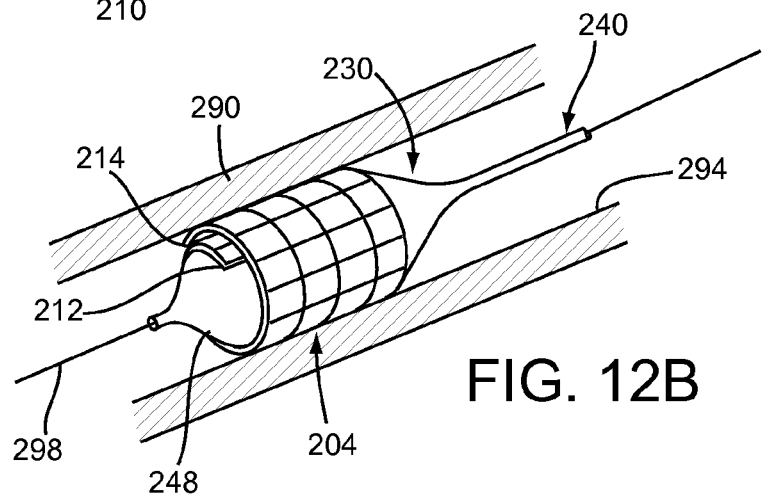
Figure 12C:
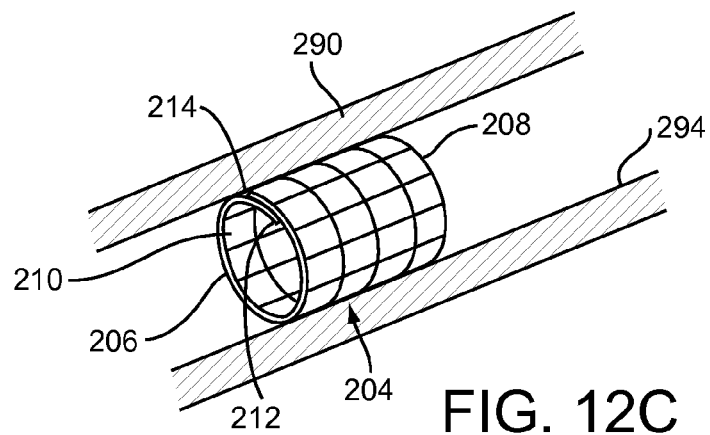

Turning to FIGS. 12A-12C, another embodiment of a structure 204 and a delivery apparatus 230 for delivering the structure 204 are shown. The structure 204 may be formed similar to the structure 4 shown in FIG. 4, e.g., from hydrogel material, using the materials and methods described above. For example, the structure 204 may be formed from freeze dried hydrogel material with or without one or more adherent layer components on an outer surface of the structure 204. Alternatively, the structure 204 may include other carriers, instead of hydrogel material, including one or more adherent layer components on the outer surface of the structure 204. Such a structure 204 may provide an in-situ patch or other endoprosthesis that may be delivered and implanted to line a wall of a vessel or other body lumen, as described further below.

In the embodiment shown, the structure 204 includes first and second ends 206, 208, a lumen 210 extending between the first and second ends 206, 208, and overlapping longitudinal edges 212, 214. The overlapping edges 212, 214 may be movable relative to one another such that structure 204 is expandable from a first contracted condition (e.g., as shown in FIG. 12A) to a second enlarged condition (e.g., as shown in FIGS. 12B and 12C), e.g., by least partially unrolling. For example, the longitudinal edges 212, 214 may overlap one another in the contracted condition to provide one or more spiral layers.

When a radially outward force is applied against an interior of the structure 204, e.g., from within the lumen 210, the longitudinal edges 212, 214 may slide circumferentially to allow the diameter of the structure 204 to increase. In the enlarged condition, the longitudinal edges 212, 214 may remain overlapped (but to a lesser extent than in the contracted condition), or the longitudinal edges 212, 214 may be spaced apart, e.g., to provide an open "C" shaped cross-section. In addition or alternatively, the structure 204 may be plastically deformed as it expands instead or in addition to unrolling.

The delivery apparatus 230 may include a catheter or other tubular member 240 including a proximal end 242, a distal end 244 sized and/or shaped for introduction into a body lumen, and a lumen 246 extending between the proximal and distal ends 242, 244. As shown, the catheter 240 may also include a balloon 248 on the distal end 244. Alternatively, the catheter 240 may include other expandable structures on the distal end, e.g., a mechanically expandable frame with or without an overlying membrane (not shown). The structure 204 may be mounted, compressed, or otherwise disposed on the distal end 244, e.g., overlying the balloon 248 (or other expandable structure).

Optionally, the delivery apparatus 230 may also include a sheath or other tubular member (not shown) that may be slidably disposed over the distal end 244 of the catheter 240. Thus, the sheath may overly the structure 204 and/or balloon 248, e.g., to facilitate advancement and/or otherwise protect the structure 204 and/or balloon 248.

The structure 204 may be made using the materials and/or methods described above, and then loaded onto the catheter 240, similar to a stent or other endoprosthesis. For example, with the balloon 248 collapsed, the structure 204 may be wrapped around the distal end 244 over the balloon 248 and compressed or crimped into the contracted condition. Alternatively, the structure 204 may be rolled, compressed, and/or crimped beforehand, and then loaded onto the distal end 244 of the catheter 240 in the contracted condition. If a sheath is provided, the sheath may be advanced over the structure 204 and distal end 244. Thus, the delivery apparatus 230 may be constructed and/or used similar to known angioplasty and/or stent delivery catheters.

Turning to FIG. 12A, during use, the apparatus 230 may be used to delivery the structure 204 to treat a stenosis, occlusion, or other lesion 290 within a blood vessel 294 or other body lumen. For example, the lesion 290 may be a site within a coronary, carotid, or other artery where atherosclerotic plaque and the like has accumulated.

With the balloon 248 collapsed and the structure 204 in the contracted condition, the distal end 244 of the catheter 240 may be introduced into a patient's vasculature, e.g., from a percutaneous entry site (not shown) over a guidewire 298. The distal end 244 may be advanced over the guidewire into the vessel 294, and positioned such that the structure 204 is disposed within the lesion 290. Optionally, the lesion 290 may be predilated or otherwise treated before introducing the structure 204, as is known in the art.

Turning to FIG. 12B, with the structure 204 disposed within the lesion 290, the balloon 248 may be inflated, thereby expanding the structure 204 to the enlarged condition, as shown. As the balloon 248 and structure 204 expand, the lesion 290 may be dilated, e.g., pushing outwardly any plaque or other material within the lesion 290, similar to angioplasty or stent delivery procedures.

Turning to FIG. 12C, once the structure 204 has been expanded to a desired size, the balloon 248 may be deflated or otherwise collapsed, and the apparatus 230 (and guidewire 298) may be removed from the patient's body, leaving the structure 204 to line the vessel 294 at the lesion 290. If the structure 204 includes one or more adherent layer components on the outer surface, the adherent layer component(s) may be exposed to blood or other fluid within the vessel 294, thereby causing the adherent layer components to react and become "sticky." Thus, the resulting adherent layer may adhere or bond the structure 204 to the wall of the vessel 294 at the lesion 290.

Optionally, one or more additional materials may be delivered into the vessel 194, e.g., via a lumen in the catheter 240 or other device (not shown). For example, if the outer surface of the structure 204 does include all of the components necessary to create an adherent layer, the other necessary components may be delivered into the vessel 294. This may initiate a reaction of the components to create the adherent layer between the structure 294 and the wall of the vessel 294, e.g., in the presence of the bodily fluids within the vessel 294. Any remaining unreacted components within the vessel 294 may be passed and/or metabolized harmlessly, without the other components provided on the structure 204 itself necessary to form the adherent layer.

Thus, the structure 204 may be used to cover various types of diseases as an in-situ patch, e.g., to treat arterial disease, arterial injury, or even arterial perforation. Optionally, the structure 204 may include one or more drugs specific to the type of disease to be addressed, e.g., to dissolve or otherwise break down plaque, prevent thrombosis or restenosis, enhance healing of the vessel wall, and the like. Thus, in addition or instead of mechanically containing cell proliferation, the structure 204 may be doped with various drugs. For example, the structure 204 may include limus and taxol-based drugs, or other anti-proliferative drug, which would inhibit cellular proliferation from the injured vessel wall.

In addition or alternative, the structure 204 (with or without one or more drugs) may be further augmented by placing a stent coaxial with the structure 204 (not shown, e.g., embedded in the structure 204, or disposed within the lumen 210), e.g., to address any elastic recoils as well as preventing cellular proliferation.

Similarly, other structures may provided, e.g., as sheets, rods, and the like (not shown), to provide multi adherent material that may be used minimally invasively in other bodily cavities, e.g., within the gastrointestinal (GI) tract, the urinary tract, the reproductive organs, and the like. Additionally, such structures may provide multi component adherent material, with or without a drug, that may be used in open surgery as an in-situ patch. Such structures may be applied by hand or using an applicator, on various sites, e.g., to treat a disease or to treat injury caused by invasive surgery.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the scope of the appended claims.

We claim:

1. A system for sealing a puncture extending through tissue, comprising:
    a cartridge comprising a tubular member sized for insertion into a puncture;
    a carrier carried within the tubular member and having a predetermined shape and sized for delivery into the puncture, the carrier formed from material configured to expand upon exposure to an aqueous physiological environment to occlude the puncture and carrying at least one adherent layer component;
    a delivery device comprising at least one additional adherent component therein and configured for delivering the at least one additional adherent layer component to the carrier in situ; and
    wherein contact between the at least one adherent layer component and the at least one additional adherent layer component in situ causes them to react with one another to create an adherent layer on the carrier,
    wherein the carrier has a lumen extending between ends of the carrier, the system further comprising a positioning member extending through the carrier lumen and the cartridge, the positioning member comprising an expandable positioning element on a distal end thereof beyond the cartridge, the positioning element expandable from a contracted condition for advancement through the puncture into the blood vessel and an expanded condition for preventing the carrier from being deployed within the blood vessel.

2. The system of claim 1, wherein the carrier comprises a bioabsorbable mass.

3. The system of claim 1, wherein the at least one adherent layer component comprises at least one of a first hydrogel precursor, a second hydrogel precursor, and an activating agent, and wherein the at least one additional adherent layer component comprises the other of the first hydrogel precursor, the second hydrogel precursor, and the activating agent that are not carried by the carrier, the first and second hydrogel precursors combining to create a hydrogel in the presence of the activating agent.

4. The system of claim 3, wherein the activating agent comprises a pH adjusting agent.

5. The system of claim 4, wherein one of the at least one adherent layer component and the at least one of additional adherent layer component further comprises ester-terminated polymer.

6. The system of claim 1, wherein the at least one adherent layer component comprises at least one of an amine-terminated polymer and an ester-terminated polymer.

7. The system of claim 6, wherein the at least one additional adherent layer component comprises the other of the amine-terminated polymer and the ester-terminated polymer.

8. The system of claim 6, wherein one of the at least one adherent layer component and the at least one of additional adherent layer component further comprises sodium borate.

9. The system of claim 1, wherein the at least one adherent layer component comprises an amine-terminated polymer.

10. The system of claim 9, wherein the amine-terminated polymer comprises a polypeptide.

11. The system of claim 1, wherein the at least one adherent layer component comprises an amine-terminated polymer and the at least one additional adherent component comprises sodium borate.

12. The system of claim 1, wherein the at least one adherent layer component comprises an ester-terminated polymer and the at least one addition adherent layer component comprises sodium borate.

13. The system of claim 1, wherein the carrier comprises a rolled sheet having a generally circular cross-sectional shape.

14. A system for sealing a puncture extending through tissue to a blood vessel, comprising:
  a cartridge comprising a tubular member sized for insertion into a puncture and a pusher member slidably disposed within the tubular member;
  a carrier disposed within the tubular member distal to the pusher member having a predetermined shape and size for sealing a puncture extending through tissue to a blood vessel, the carrier formed from material configured to expand upon exposure to an aqueous physiological environment to occlude the puncture and carrying at least one adherent layer component;
  a delivery device comprising at least one additional adherent component therein and configured for delivering the at least one additional adherent layer component to the carrier in situ via the cartridge; and
  wherein contact between the at least one adherent layer component and the at least one additional adherent layer component in situ causes them to react with one another to create an adherent layer on the carrier,
  wherein the carrier has a lumen extending between ends of the carrier, the system further comprising a positioning member extending through the carrier lumen and the cartridge, the positioning member comprising an expandable positioning element on a distal end thereof beyond the cartridge, the positioning element expandable from a contracted condition for advancement through the puncture into the blood vessel and an expanded condition for preventing the carrier from being deployed within the blood vessel.

15. The system of claim 14, wherein the delivery device comprises a syringe coupled to at least one of the tubular member and the pusher member for delivering the at least one additional adherent layer component to the carrier.

16. The system of claim 14, wherein the at least one adherent layer component comprises at least one of a first hydrogel precursor, a second hydrogel precursor, and an activating agent, and wherein the at least one additional adherent layer component comprises the other of the first hydrogel precursor, the second hydrogel precursor, and the activating agent that are not carried by the carrier, the first and second hydrogel precursors combining to create a hydrogel in the presence of the activating agent.

17. The system of claim 14, wherein the carrier comprises a rolled sheet having a generally circular cross-sectional shape.

18. The system of claim 14, wherein the carrier is bioabsorbable.

19. A system for sealing a puncture extending through tissue to a body lumen, comprising:
  a generally cylindrical core having a size and shape for delivery into the puncture, the core comprising bioabsorbable material configured to expand upon exposure to an aqueous physiological environment to occlude the puncture and carrying at least one adherent layer component;
  a delivery device comprising at least one additional adherent component therein and configured for delivering the at least one additional adherent layer component to the core in situ; and
  wherein contact between the at least one adherent layer component and the at least one additional adherent layer component in situ causes them to react with one another to create an adherent layer on the core to enhance retention of the expanded core within the puncture,
  wherein the core has a lumen extending between ends of the core, the system further comprising a positioning member extending through the core lumen, the positioning member comprising an expandable positioning element on a distal end thereof, the positioning element expandable from a contracted condition for advancement through the puncture into the blood vessel and an expanded condition for preventing the core from being deployed within the blood vessel.

20. The system of claim 19, wherein the core comprises a rolled sheet having a generally circular cross-sectional shape.

* * * * *